US006764858B2

(12) United States Patent
Stockman

(10) Patent No.: US 6,764,858 B2
(45) Date of Patent: Jul. 20, 2004

(54) METHODS FOR CREATING A COMPOUND LIBRARY

(75) Inventor: Brian J. Stockman, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/044,219

(22) Filed: Nov. 19, 2001

(65) Prior Publication Data

US 2002/0192707 A1 Dec. 19, 2002

Related U.S. Application Data

(63) Continuation-in-part of application No. 09/677,107, filed on Sep. 29, 2000.
(60) Provisional application No. 60/156,818, filed on Sep. 29, 1999, provisional application No. 60/161,682, filed on Oct. 26, 1999, and provisional application No. 60/192,685, filed on Mar. 28, 2000.

(51) Int. Cl.[7] .................... G01N 24/00; G01N 33/566; G01N 33/543; G01N 33/53; C07K 17/00
(52) U.S. Cl. ................. 436/173; 435/7.1; 435/DIG. 2; 435/DIG. 14; 435/DIG. 15; 435/DIG. 20; 436/501; 436/518; 530/350
(58) Field of Search .......................... 435/7.1, DIG. 2, 435/14, 15, 20; 436/501, 518, 173; 530/350

(56) References Cited

U.S. PATENT DOCUMENTS

| | | | |
|---|---|---|---|
| 4,719,582 A | 1/1988 | Ishida et al. | |
| 5,270,163 A | 12/1993 | Gold et al. | |
| 5,306,619 A | 4/1994 | Edwards et al. | |
| 5,668,734 A | 9/1997 | Krishna et al. | |
| 5,698,401 A | 12/1997 | Fesik et al. | |
| 5,804,390 A | 9/1998 | Fesik et al. | |
| 5,837,460 A | 11/1998 | Von Feldt et al. | |
| 5,856,496 A | 1/1999 | Fagnola et al. | |
| 5,891,643 A | 4/1999 | Fesik et al. | |
| 5,989,827 A | 11/1999 | Fesik et al. | |
| 6,043,024 A | 3/2000 | Fesik et al. | |
| 6,214,561 B1 | 4/2001 | Peters et al. | |

FOREIGN PATENT DOCUMENTS

| | | |
|---|---|---|
| DE | 196 49 359 C1 | 2/1998 |
| EP | 0 592816 A1 B1 | 4/1994 |
| GB | 2 316 941 A | 3/1998 |
| GB | 2 321 104 A | 7/1998 |
| WO | WO 91/10140 | 7/1991 |
| WO | WO 91/17428 | 11/1991 |
| WO | WO 93/00446 | 1/1993 |
| WO | WO 94/14980 | 7/1994 |
| WO | WO 96/30849 | 10/1996 |
| WO | WO 97/00244 | 1/1997 |
| WO | WO 97/18469 | 5/1997 |
| WO | WO 97/18471 | 5/1997 |
| WO | WO 98/46548 | 10/1998 |
| WO | WO 98/48264 | 10/1998 |
| WO | WO 98/57155 | 12/1998 |
| WO | WO 99/09024 | 2/1999 |
| WO | WO 99/17616 | 4/1999 |
| WO | WO 99/36422 | 7/1999 |
| WO | WO 99/43643 | 9/1999 |

OTHER PUBLICATIONS

Ajay et al., "Can We Learn To Distinguish between "Drug–like" and "Nondrug–like" Molecules?", *J. Med. Chem.*, 41:3314–3324 (1998).

Anderson et al., "Affinity NMR: Decoding DNA Binding," *Journal of Combinatorial Chemistry*, 1(1):69–72 (1999).

Balaram et al., "Localization of Tyrosine at the Binding Site of Neurophysin II by Negative Nuclear Overhauser Effects", *Journal of the American Chemical Society*, 94:11:4017–4018 (1972).

Barjat et al., "High–Resolution Diffusion–Ordered 2D Spectroscopy (HR–DOSY) —A New Tool for the Analysis of Complex Mixtures," *Journal of Magnetic Resonance, Series B*, 108:170–172 (1995).

Bax et al., "Sensitivity–Enhanced Two–Dimensional Heteronuclear Shift Correlation NMR Spectroscopy," *Journal of Magnetic Resonance*, 67:565–569 (1986).

Belton et al., "Application of chemometrics to the $^1$H NMR spectra of apple juices: discrimination between apple varieties," *Food Chemistry*, 61:207–213 (1998).

Bemis et al., "The Properties of Known Drugs. 1. Molecular Frameworks," *J. Med. Chem.*, 39:2887–2893 (1996).

Bemis et al., "Properties of Known Drugs. 2. Side Chains," *J. Med. Chem.*, 42:5095–5099 (1999).

BLAST 2 Sequences. [online] National Center for Biotechnology Information, National Institutes of Health, United States, [retrieved Aug. 29, 2001]. Retrieved from the Internet: <URL:http://www.ncbi.nlm.nih.gov/gorf/bl2.html>, 1 page.

Bleicher et al., "Diffusion Edited NMR: Screening Compound Mixtures by Affinity NMR to Detect Binding Ligands to Vancomycin," *Journal of Organic Chemistry*, 63(23):8486–8490 (1998).

Boguslavsky, "NMR Finds Elusive Protein–Binding Molecules," *Drug Discovery & Development*, 56–60 (1999).

Bothner–By et al., "Binding of Small Molecules to Proteins," *Ann. NY Acad. Sci.*, 222:668–675 (1973).

(List continued on next page.)

*Primary Examiner*—Maurie Garcia Baker
(74) *Attorney, Agent, or Firm*—Mueting, Raasch & Gebhardt, P.A.

(57) ABSTRACT

A method for developing a library of compounds, the compound library, a method for identifying ligands for target molecules, and a method for identifying lead chemical templates, which, for example, can be used in drug discovery and design are provided. Certain embodiments of these methods include the use of NMR spectroscopy.

9 Claims, 21 Drawing Sheets

OTHER PUBLICATIONS

Bruker http://www.bruker.de/analytic/nmr-dep/best/best.htm.

Bussiere et al., "Structure of the E2 DNA–Binding Domain form Human Papillomavirus Serotype 31 at 2.4 Å," *Acta Crystallographica, D54* (Part 6, No. 2):1367–1376 (1998).

Chen et al., "NOE Pumping: A Novel NMR Technique for Identification of Compounds with Binding Affinity to Macromolecules," *Journal of the American Chemical Society, 120*(39):10258–10259 (1998).

Chen et al., "NOE Pumping. 2. A High–Throughput Method To Determine Compounds with Binding Affinity to Macromolecules by NMR," *J. Am. Chem. Soc., 122*:414–415 (2000).

Chiyoda et al., "Screening System for Urease Inhibitors Using $^{13}$C–NMR," *Chemical & Pharmaceutical Bulletin, 46*(4):718–720 (1998).

Dalvit et al., "Use of organic solvents and small molecules for locating binding sites on proteins in solution," *Journal of Biomolecular NMR, 14*(1):23–32 (1999).

Dalvit et al., "Identification of compounds with binding affinity to proteins via magnetization transfer from bulk water," *Journal of Biomolecular NMR 18*:65–68 (2000).

Delaglio, "Adaptive Analysis and Multivariate Methods for Applications," *NMR Technologies: Development and Applications for Drug Discovery*, Sheraton Inner Harbor Hotel, Baltimore, MD (Nov. 4–5, 1999).

Detlefsen et al., "Molecular Flexibility Profiling Using NMR Spectroscopy," *Current Medicinal Chemistry, 6*(5):353–358 (1999).

Fairbanks et al., "Purification and structural characterization of the CD11b/CD18 integrin α subunit I domain reveals a folded conformation in solution," *FEBS Letters, 369*(2–3):197–201 (1995).

Farley et al., "SMASH: Small Molecule NMR Conference," Presentation Materials for SMASH '99, Argonne, IL (Aug. 15–18, 1999).

Farmer II et al., "Localizing the NADP$^+$ binding site on the MurB enzyme by NMR," *Nature Structural Biology, 3*(12):995–997 (1996).

Fecik et al., "The Search for Orally Active Medications Through Combinatorial Chemistry," *Medicinal Research Reviews, 18*:149–185 (1998).

Fejzo et al., "The SHAPES Strategy: An NMR Based Approach for Lead Generation in Drug Discovery," Abstract MIIA–4, *Proceedings of the 18th International Conference on Magnetic Resonance in Biological Systems*, Tokyo Metropolitan University, Tokyo, Japan, 3 pages (Aug. 23–28, 1998).

Fejzo et al., "The SHAPES strategy: an NMR–based approach for lead generation in drug discovery," *Chemistry & Biology, 6*:755–769 (1999).

Fesik, "NMR structure–based drug design," *Journal of Biomolecular NMR, 3*(3):261–269 (1993).

Freeman et al., "Proton–detected $^{15}$N NMR spectroscopy and imaging," EPO abstract, XP 002029543, from *Journal of Magentic Resonance, Series B, 102*(2):183–192, 1 page (1993).

Freeman et al., "Proton–Detected $^{15}$N NMR Spectroscopy and Imaging," *Journal of Magnetic Resonance, Series B, 102*(2):183–192 (1993).

Ghose et al., "A Knowledge–Based Approach in Designing Combinatorial or Medicinal Chemistry Libraries for Drug Discovery. 1. A Qualitative and Quantitative Characterization of Known Drug Databases," *J. Comb. Chem., 1*: 55–68 (1999).

Gonnella et al., "Isotope–Filtered Affinity NMR," *Journal of Magnetic Resonance, 131*:336–338 (1998).

Gounarides et al., "Nuclear magnetic resonance chromatography: applications of pulse field gradient diffusion NMR to mixture analysis and ligand–receptor interactions," *Journal of Chromatography B, 725*(1):79–90 (1999).

Grzesiek et al., "The Importance of Not Saturating H$_2$O in Protein NMR. Application to Sensitivity Enhancement and NOE Measurements," *Journal of the American Chemical Society, 115*(26):12593–12594 (1993).

Hajduk et al., "High–Throughput Nuclear Magnetic Resonance–Based Screening," *J. Med. Chem., 42*:2315–2317 (1999).

Hajduk et al., "One Dimensional Relaxation– and Diffusion–Edited NMR Methods for Screening Compounds That Bind to Macromolecules," *J. Am. Chem. Soc., 119*:12257–12261 (1997).

Hajduk et al., "NMR–based discovery of lead inhibitors that block DNA binding of the human papillomavirus E2 protein," *J. Med. Chem.40*(20):3144–50 (1997).

Hegde et al., "Crystal structure at 1.7 • of the bovine papillomavirus–1 E2 DNA–binding domain bound to its DNA target," *Nature, 359*(6395):505–512 (1992).

Hegde et al., "Crystal Structure of the E2 DNA–binding Domain from Human Papillomavirus Type 16: Implications for its DNA Binding–site Selection Mechanism," *Journal of Molecular Biology, 284*(5):1479–1489 (1998).

Henrichsen et al., "Bioaffinity NMR spectroscopy: identification of an E–selectin antagonist in a substance mixture by transfer NOE," *Angewandte Chemie, International Edition, 38*(1/2):98–102 (1999).

Holmes et al., "Development of a model for classification of toxin–induced lesions using $^1$H NMR spectroscopy of urine combined with pattern recognition," *NMR in Biomedicine, 11*:235–244 (1998).

Kasukawa et al., "A Fifteen–Amino–Acid Peptide Inhibits Human Papillomavirus E1–E2 Interaction and Human Papillomarivus DNA Replication In Vitro," *Journal of Virology, 72*(10):8166–8173 (1998).

Keifer, "High–resolution NMR techniques for solid–phase synthesis and combinatorial chemistry," *Drug Discovery Today*, 2:468–478 (1997).

Keifer, "NMR tools for biotechnology," *Current Opinion in Biotechnology, 10*:34–41, (1999).

Keifer et al., "Direct–Injection NMR (DI–NMR): A Flow NMR Technique for the Analysis of Combinatorial Chemistry Libraries[1]," *J. Comb. Chem., 2*:151–171 (2000).

Keifer, "New methods for obtaining high–resolution NMR spectra of solid–phase synthesis resins, natural products, and solution–state combinatorial chemistry libraries," *Drugs of the Future, 23*:301–317 (1998).

Kulkov et al., "Searching NMR Databases and Predicting NMR Spectra Over the Web," Abstract 71, *Abstracts of Papers, Part 1, 218th ACS National Meeting*, American Chemical Society, New Orleans, LA, (Aug. 22–26, 1999).

Lennon et al., "Hemoglobin Affinity for 2,3–Bisphosphoglycerate in Solutions and Intact Erythrocytes: Studies Using Pulsed–Field Gradient Nuclear Magnetic Resonance and Monte Carlo Simulations," *Biophysical Journal*, 67:2096–2109 (1994).

Liang et al., "Solution Structure of the DNA–Binding Domain of a Human Papillomarivus E2 Protein: Evidence for Flexible DNA–Binding Regions," *Biochemistry*, 35(7):2095–2103 (1996).

Liepinsh et al., "Organic solvents identify specific ligand binding sites on protein surfaces," *Nature Biotechnology*, 15(3):264–268 (1997).

Lin et al., "Diffusion–Edited NMR–Affinity NMR for Direct Observation of Molecular Interactions," *J. Am. Chem. Soc.*, 119:5249–5250 (1997).

Lin et al., "Screening Mixtures by Affinity NMR," *J. Org. Chem.*, 62:8930–8931 (1997).

Lindon et al., "Direct coupling of chromatographic separations to NMR spectroscopy," *Progress in Nuclear Magnetic Resonance Spectroscopy*, 29:1–49 (1996).

Lindon et al., "Directly Coupled HPLC–NMR and Its Application to Drug Metabolism," *Drug Metabolism Reviews*, 29:705–746 (1997).

Lipinski et al., "Experimental and computational approaches to estimate solubility and permeability in drug discovery and development settings," *Advanced Drug Delivery Reviews*, 23:3–25 (1997).

Liu et al., "High–Resolution Diffusion and Relaxation Edited One– and Two–Dimensional $^1$H NMR Spectroscopy of Biological Fluids," *Analytical Chemistry*, 68(19):3370–3376 (1996).

Martin et al., "Beyond Mere Diversity: Tailoring Combinatorial Libraries for Drug Discovery," *J. Comb. Chem.*, 1:32–45 (1999).

Mazel et al., "Genetic characterization of polypeptide deformylase, a distinctive enzyme of eubacterial translation," *The EMBO Journal*, 13:914–923 (1994).

McBride et al., "The Papillomavirus E2 Regulatory Proteins," *The Journal of Biological Chemistry*, 266(28):18411–18414 (1991).

Meyer et al., "Screening mixtures for biological activity by NMR," *Eur. J. Biochem.*, 246:705–709 (1997).

Moore, "NMR screening in drug discovery," *Current Opinion in Biotechnology*, 10(1):54–58 (1999).

Moore, "NMR Techniques for Characterization of Ligand Binding: Utility for Lead Generation and Optimization in Drug Discovery," *Biopolymer (Peptide Science*, 51:221–243 (1999).

Morris et al., "Diffusion–Ordered Two–Dimensional Nuclear Magnetic Resonance Spectroscopy," *Journal of the American Chemical Society*, 114(8):3139–3141 (1992).

Morris et al., "Resolution of Discrete and Continuous Molecular Size Distributions by Means of Diffusion–Ordered 2D NMR Spectroscopy," *Journal of the American Chemical Society*, 115(10):4291–4299 (1993).

Neri et al., "$^1$H, $^{13}$C and $^{15}$N backbone assignments of cyclophilin when bound to cyclosporin A (CsA) and preliminary structural characterization of the CsA binding site," *FEBS Letters*, 294(1,2):81–88 (1991).

Nicholson et al., "'Metabonomics': understanding the metabolic responses of living systems to pathophysiological stimuli via multivariate statistical analysis of biological NMR spectroscopic data," *Xenobiotica*, 29:1181–1189 (1999).

Pearlman et al., "Novel Software Tools for Chemical Diversity," *Perspectives in Drug Discovery and Design* 09/10/11:339–353 (1998).

Phelps et al., "Molecular targets for human papillomaviruses: prospects for antiviral therapy," *Antiviral Chemistry & Chemotherapy*, 9(5):359–377 (1998).

Piotto et al., "Gradient–tailored excitation for single–quantum NMR spectroscopy of aqueous solutions," *Journal of Biomolecular NMR*, 2(6):661–665 (1992).

Ponstingle et al., "Detection of protein–ligand NOEs with small, weakly binding ligands by combined relaxation and diffusion filtering," *Journal of Biomolecular NMR*, 9:441–444 (1997).

Rabenstein et al., "A Pulse Sequence for the Measurement of Spin–Lattice Relaxation Times of Small Molecules in Protein Solutions," *Journal of Magnetic Resonance*, 34:669–674 (1979).

Ross et al., "Fast–HMQC using Ernst angle pulses: An efficient tool for screening of ligand binding to target proteins," *Journal of Biomolecular NMR*, 10:389–396 (1997).

Ross et al., "Automation of NMR measurements and data evaluation for systematically screening interactions of small molecules with target proteins," *Journal of Biomolecular NMR*, 16:139–146 (2000).

Sadowski et al., "A Scoring Scheme for Discriminating between Drugs and Nondrugs," *J. Med. Chem.*, 41:3325–3329 (1998).

Scherf et al., "A $T_{1\rho}$–filtered two–dimensional transferred NOE spectrum for studying antibody interactions with peptide antigens," *Biophysical Journal*, 64:754–761 (1993).

Shapiro et al., "High resolution NMR for screening ligand/protein binding," *Current Opinion in Drug Discovery & Development*, 2:396–400 (1999).

Shuker, "Discovering High–Affinity Ligands for Proteins: SAR by NMR," *Science*, 274:1531–1534 (1996).

Spraul et al., "High–Throughput Flow–Injection NMR and its Applications," *Bruker Report*, Bruker Analytik GmbH, Rheinstetten, Germany, (Aug./Sep. 1999).

Spraul et al., "Flow Injection Proton Nuclear Magnetic Resonance Spectroscopy Combined With Pattern Recognition Methods: Implications for Rapid Structural Studies and High Througput Biochemical Screening," *Analytical Communications*, 34:339–341 (1997).

Stilbs, "Molecular Self–Diffusion Coefficients in Fourier Transform Nuclear Magnetic Resonance Spectrometric Analysis of Complex Mixtures," *Analytical Chemistry*, 53(13):2135–2137 (1981).

Stockman, "NMR spectroscopy as a tool for structure–based drug design," *Progress in Nuclear Magnetic Resonance Spectroscopy*, 33:109–151 (1998).

Stockman, "Flow NMR spectroscopy in drug discovery," *Current Opinion in Drug Discovery & Development*, 3:269–274 (2000).

Stockman et al., "$^1$H and $^{15}$N resonance assignments and solution secondary structure of oxidized *Desulfovibrio vulgaris* flavodoxin determined by heteronuclear three–dimensional NMR spectroscopy," *J. Biol. NMR*, 3:133–149 (1993).

Stockman, "Applications of flow NMR spectroscopy to monitor binding of small molecules to proteins," Innovative Computational Applications: The Interface of Library Design, Bioinformatics, Structure Based Drug Design and Virtual Screening, Biotechnology Division, Institute for International Research, San Francisco, CA, Oct. 25–27, 1999.

Stockman, "Applications of flow NMR spectroscopy to monitor binding fo small molecules to proteins," NMR Technologies: Development and Applications for Drug Discovery, Cambridge Healthtech Institute's Second International, Baltimore, MD, Nov. 4–5, 1999.

Stockman, "Applications of flow NMR spectroscopy to monitor binding of small molecules to proteins," NMR in the drug discovery pipeline, IBC, London, UK, May 8–9, 2000.

Stockman et al., "Screening of compound libraries for protein binding using flow–injection nuclear magnetic resonance spectroscopy," *Methods Enzymol.* 2001;338:230–46.

Tatusova et al., "BLAST 2 Sequences, a new tool for comparing protein and nucleotide sequences," *FEMS Microbiology Letters*, 174(2):247–250 (1999).

Teague et al., "The Design of Leadlike Combinatorial Libraries," *Angew. Chem. Int. Ed.*, 38:3743–3748 (1999).

Veeraraghavan et al., "$^{1}$H, $^{15}$N, and $^{13}$C NMR resonance assignments for the DNA–binding domain of the BPV–1 E2 protein," *Journal of Biomolecular NMR*, 11(4):457–458 (1998).

Veeraraghavan et al., "Structural correlates for enhanced stability in the E2 DNA–binding domain from bovine papillomavirus," *Biochemistry*, 38(49):16115–24 (1999).

Vogler et al., "Rapid Communications," *Journal of Natural Products*, 61:175–178 (1998).

Wang et al., "Solution Studies of Staphylococcal Nuclease H124L. 2. $^{1}$H, $^{13}$C, and $^{15}$N Chemical Shift Assignments for the Unligated Enzyme and Analysis of Chemical Shift Changes that Accompany Formation of the Nuclease–Thymidine 3', 5'–Bisphosphate–Calcium Ternary Complex†,‡", *Biochemistry*, 31:921–936 (1992).

Wang et al., "Toward Designing Drug–Like Libraries: A Novel Computational Approach for Prediction of Drug Feasibility of Compounds," *J. Comb. Chem.*, 1:524–533 (1999).

Warr, "Combinatorial Chemistry and Molecular Diversity. An Overview," *J. Chem. Inf. Comput. Sci.*, 37, 134–140 (1997).

Watanabe et al., "Direct–Coupling of FT–NMR to High Performance Liquid Chromatography," *Proc. Japan Acad. Ser B*, 54:194–199 (1978).

Watt et al., "Comparison of the crystal structures of a flavodoxin in its three oxidation states at cryogenic temperatures," *J. Mol. Biol.*, 218:195–208 (1991).

Wider et al., "Proton–proton Overhauser effects of receptor–bound cyclosporin A observed with the use of a heteronuclear–resolved half–filter experiment," EPO abstract, XP 002029543, from *Journal of the American Chemical Society*, 113(12):4676–4678, 2 pages (1991).

Wider et al., "Proton–Proton Overhauser Effects of Receptor–Bound Cyclosporin A Observed with the Use of a Heteronuclear–Resolved Half–Filter Experiment," *Journal of the American Chemical Society*, 113(12):4676–4678 (1991).

Wider, "Structure Determination of Biological Macromolecules in Solution Using Nuclear Magnetic Resonance Spectroscopy," *BioTechniques*, 29(6):1278–1294 (2000).

Wishart et al., "The $^{13}$C Chemical–Shift Index: A simple method for the identification of protein secondary structure using $^{13}$C chemical–shift data," *Journal of Biomolecular NMR*, 4(2):171–180 (1994).

Wishart et al, "Protein chemical shift analysis: a practical guide" *Biochemistry and Cell Biology*, 76(2/3):153–163 (1998).

Wolfender et al., "LC/NMR in Natural Products Chemistry," *Current Organic Chemistry*, 2:575–596 (1998).

Wu et al., "An improved diffusion–ordered spectroscopy experiment incorporating bipolar–gradient pulses," *J. Magn. Reson. Ser. A*, 115:260–264 (1995).

Dalvit et al., "Sensitivity–improved detection of protein hydration and its extension to the assignment of fast–exchanging resonances," *J. Magn. Reson. B.*, 109:334–338 (1995).

Dalvit, "Homonuclear 1D and 2D NMR Experiments for the Observation of Solvent–Solute Interactions," *J Magn Reson B*. Sep. 1996;112(3):282–288. (No abstract available.).

Dalvit et al., "Half–filter experiments for assignment, structure determination and hydration analysis of unlabelled ligands bound to $^{13}$C/$^{15}$N labelled proteins," *J. Biomol. NMR*, 13:43–50 (1999).

Hajduk et al., "Integration of NMR and high–throughput screening," *Comb Chem High Throughput Screen*, Dec.;5(8):613–621 (2002).

Hwang et al., "Water suppression that works. Excitation sculpting using arbitrary waveforms and pulsed field gradients," *J. Magn. Reson. A112*:275–279 (1995).

Kallen et al., "Structural basis for LFA–1 inhibition upon lovastatin binding to the CD11a I–domain," *J. Mol. Biol.*, 292:1–9 (1999).

Melacini et al., "Band–selective editing of exchange–relay in protein–water NOE experiments," *J. Biomol. NMR*, 13:67–71 (1999a).

Melacini et al., "Water–macromolecule interactions by NMR: a quadrature–free constant–time approach and its application to C12," *J. Biomol. NMR*, 15:189–201 (1999b).

Otting et al., "Studies of protein hydration in aqueous solution by direct NMR observation of individual protein–bound water molecules," *J. Am. Chem. Soc.*, 111:1871–1875 (1989).

Otting et al., "Protein hydration in aqueous solution by direct NMR observation of individual protein–bound water molecules," *Science*, 254(5034): 974–980 (1991).

Otting, "NMR studies of water bound biological molecules," *Progr. NMR Spectrosc.*, 31:259–285 (1997).

Price, "Water signal suppression in NMR spectroscopy," *Annual Reports on NMR Spectroscopy* (Ed., Webb, A.), Academic Press, New York, vol. 38, pp. 289–354 (1999).

Sobol et al., "Solvent magnetization artifacts in high–field NMR studies of macromolecules hydration," *J Magn Reson*. Feb. 1998;130(2):262–271.

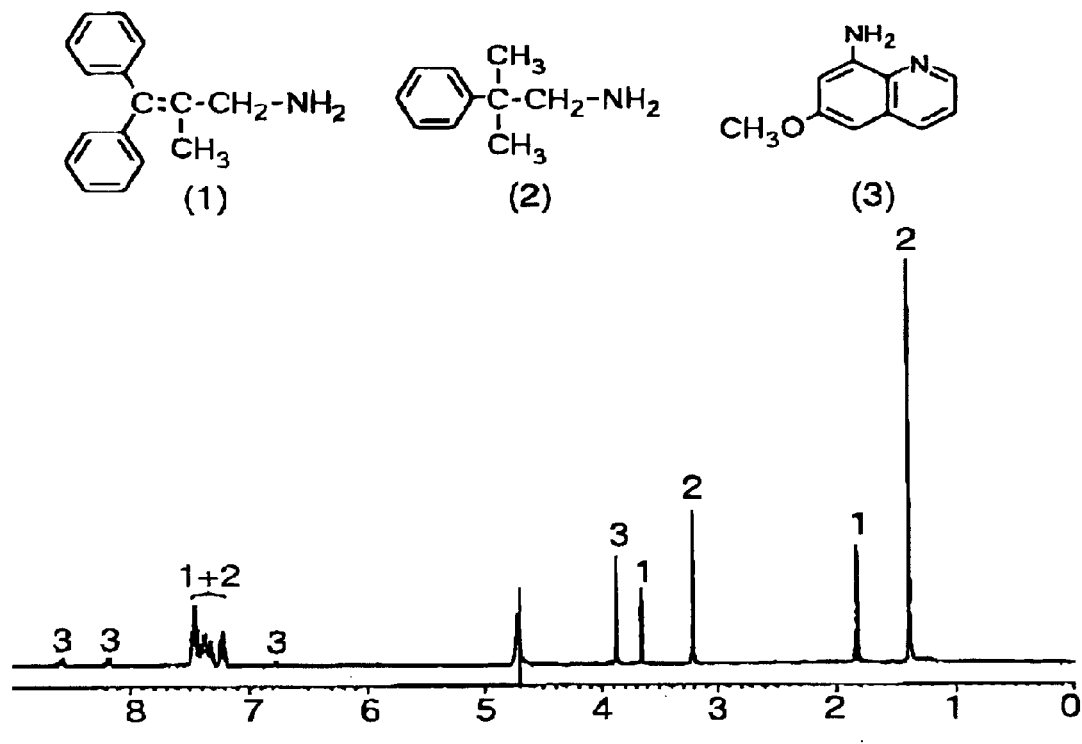
Fig. 3A
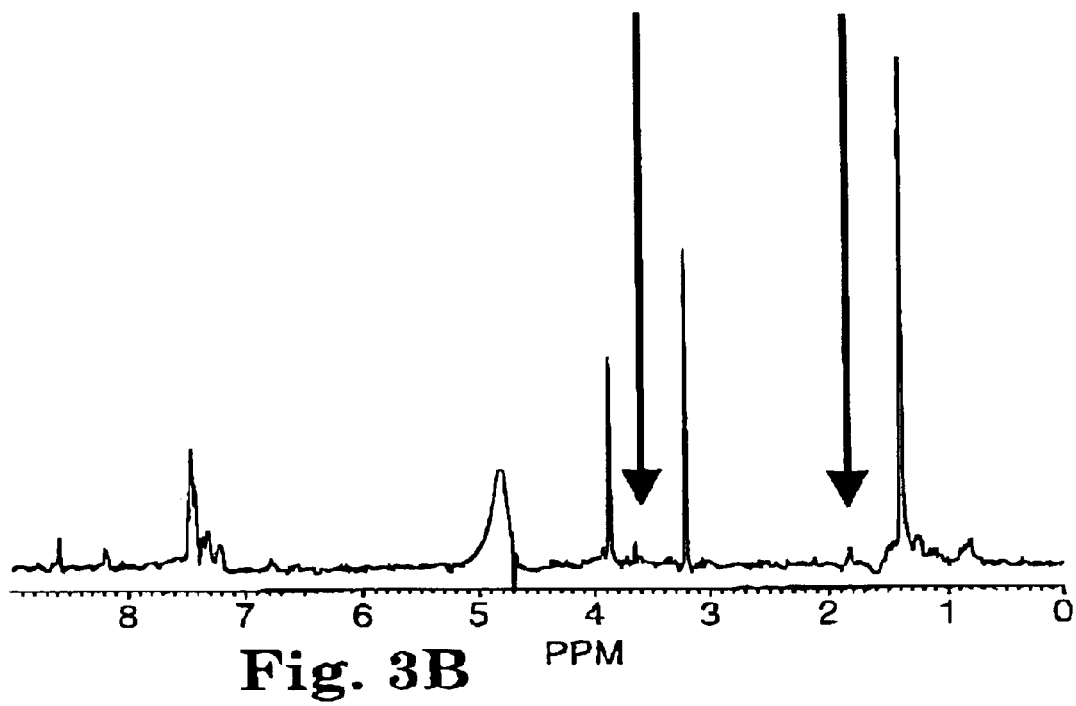
Fig. 3B  PPM

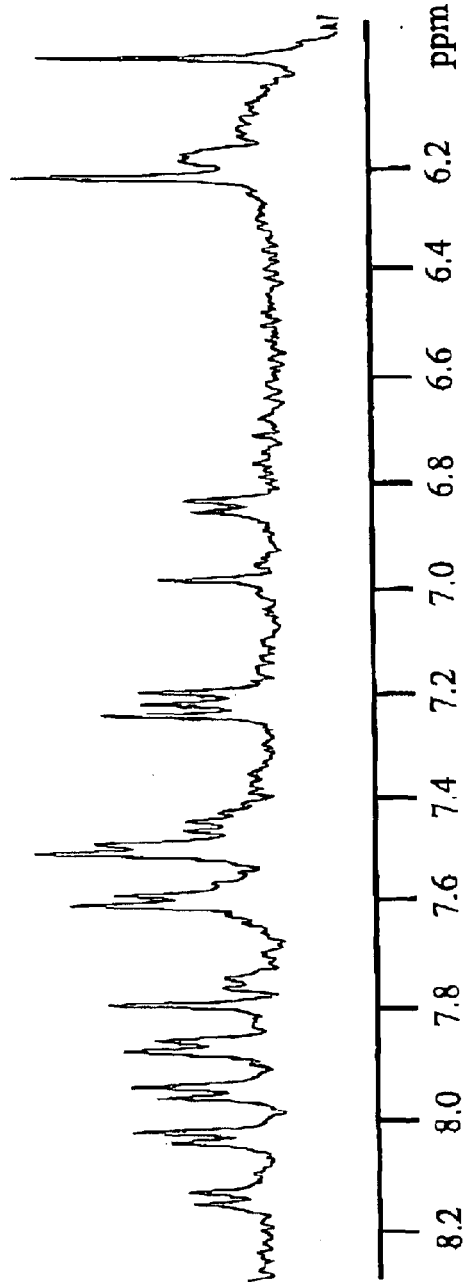
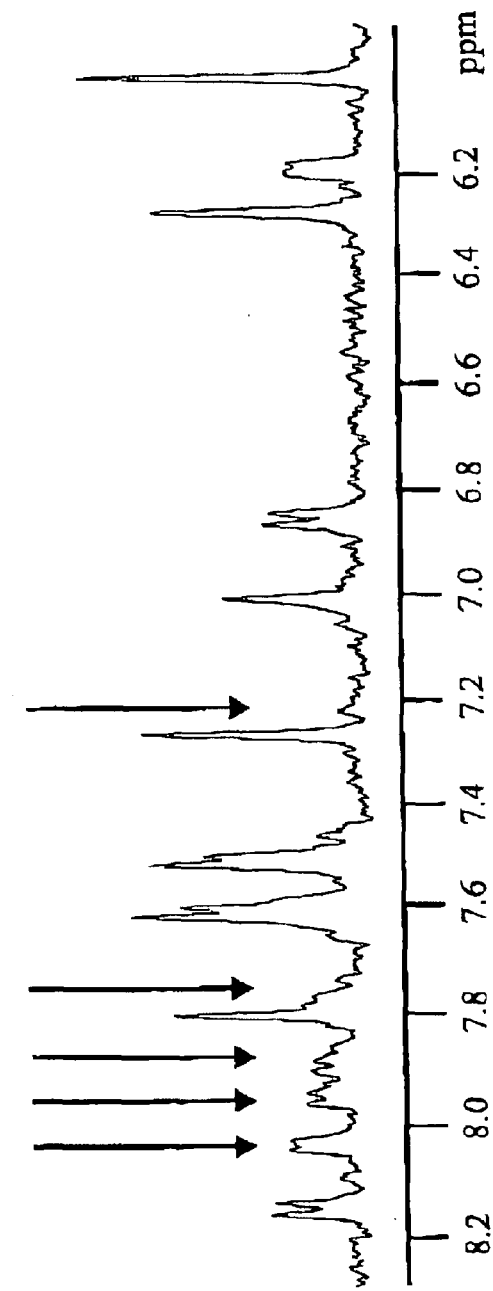
Fig. 8A
Fig. 8B

METHODS FOR CREATING A COMPOUND LIBRARY

CROSS-REFERENCE TO RELATED APPLICATIONS

The present application is a continuation-in-part of U.S. application Ser. No. 09/677,107 filed on Sep. 29, 2000, which claims the benefit of Ser. No. 60/156,818, filed on Sep. 29, 1999, No. 60/161,682, filed on Oct. 26, 1999, and No. 60/192,685, filed on Mar. 28, 2000, each of which is incorporated herein by reference in its entirety.

BACKGROUND OF THE INVENTION

From an organic chemistry standpoint, the process of drug design can be considered to involve two steps. First, a lead chemical template (often one or more) is selected. Second, a synthetic chemistry effort is undertaken to create analogs of the lead chemical template to create a compound or compounds possessing the desired therapeutic and pharmacokinetic properties.

An important step in the drug discovery process is the selection of a suitable lead chemical template upon which to base a chemistry analog program. The process of identifying a lead chemical template for a given molecular target typically involves screening a large number of compounds (often more than 100,000) in a functional assay, selecting a subset based on some arbitrary activity threshold for testing in a secondary assay to confirm activity, and then assessing the remaining active compounds for suitability of chemical elaboration.

This process can be quite time- and resource-consuming, and has numerous disadvantages. It requires the development and implementation of a high-throughput functional assay, which by definition requires that the function of the molecular target be known. It requires the testing of large numbers of compounds, the vast majority of which will be inactive for a given molecular target. It leads to the depletion of chemical resources and requires the continual maintenance of large collections of compounds. Importantly, it often leads to a final pool of potential lead templates that for the most part, with the exception of affinity for a given molecular target, do not possess desirable drug-like qualities. In some cases, high-throughput functional assays do not identify any compounds from the large number (e.g., 100,000) of compounds screened that meet the criteria established for activity.

Thus, what is needed is a faster and better approach to identifying a lead chemical template.

SUMMARY OF THE INVENTION

The present invention is related to rational drug design. Specifically, the present invention provides an approach to the development of a library of compounds as well as methods for identifying compounds (e.g., ligands) that bind to a specific target molecule (e.g., proteins) and lead chemical templates that can be used, for example, in drug discovery and design. Significantly and preferably, this approach for identifying ligands for target molecules (e.g., proteins) uses nuclear magnetic resonance (NMR) spectroscopy. There are numerous NMR spectroscopic techniques currently available that detect binding of small molecules to targets such as protein targets, including targets identified using genomics techniques that lack a functional assay. Ligands with only moderate binding affinities, which might be overlooked in a traditional functional assay but yet might serve as templates for subsequent synthetic chemistry efforts, can potentially be identified using the present invention. Preferably, one method of the present invention involves the use of flow NMR techniques, which can reduce the amount of time and effort required to evaluate small molecules for binding to a given target.

In one aspect, the present invention provides a method of creating a chemical compound library, and the library itself. The method includes: selecting compounds having a molecular weight of no greater than about 350 grams/mole; and selecting compounds having a solubility in deuterated water of at least about 1 mM at room temperature. Preferably, a majority (i.e., greater than 50%) of the compounds in the chemical compound library have a molecular weight of no greater than about 350 grams/mole and a solubility in deuterated water of at least about 1 mM at room temperature. More preferably, at least about 75% of the compounds, and most preferably, all of the compounds in the chemical compound library have a molecular weight of no greater than about 350 grams/mole and a solubility in deuterated water of at least about 1 mM at room temperature. Preferably, this library of compounds includes at least about 75 compounds, more preferably, at least about 300 compounds, and most preferably, at least about 2000 compounds, and have relatively diverse chemical structures. Herein, the molecular weights of the compounds are determined without solubilizing counterions (if the compounds are salts) and without water molecules of hydration. Also, concentrations are reported based on aqueous solutions, which may or may not include a buffer.

In another embodiment, the present invention provides a method of identifying a lead chemical template (of which there often may be one or more), for example, for designing a bioactive agent such as a drug (e.g., a compound having therapeutic and/or prophylactic capabilities). The method includes: selecting compounds having a molecular weight of no greater than about 350 grams/mole, and a solubility in deuterated water of at least about 1 mM at room temperature to create a chemical compound library; identifying at least one compound from the library that functions as a ligand (i.e., a compound that binds to a target molecule) having a dissociation constant to a target molecule (e.g., protein) of no weaker than (i.e., at least) about 100 $\mu$M; and using the ligand to identify a lead chemical template, which can be used, for example, for designing a drug. Preferably, the lead chemical template has a dissociation constant to a target molecule (e.g., protein) of no weaker than (i.e., at least) about 1 $\mu$M. Preferably, the lead chemical template can be identified through further screening efforts or through direct chemical elaborations. Preferably, a majority (i.e., greater than 50%) of the compounds in the chemical compound library, more preferably, at least about 75%, and most preferably, all of the compounds in the chemical compound library, have a molecular weight of no greater than about 350 grams/mole and a solubility in deuterated water of at least about 1 mM at room temperature.

Another embodiment of the present invention provides a method of identifying a compound that binds to a target molecule (e.g., protein). The method includes: providing a plurality of mixtures of test compounds, each mixture being in a (separate) sample reservoir (preferably, a sample reservoir of a multiwell sample holder (e.g., a 96-well microtiter plate)); introducing a target molecule (e.g., protein) into each of the sample reservoirs to provide a plurality of test samples; providing a nuclear magnetic spectrometer equipped with a flow-injection probe; transferring each test sample from the sample reservoir into the flow-injection probe; collecting a relaxation-edited (preferably, a one-dimensional (1D) relaxation-edited) nuclear magnetic resonance spectrum (preferably, a $^1$H NMR spectrum) on each sample in each reservoir; and comparing the spectra of each sample to the spectra taken under the same conditions in the absence of the target molecule (e.g., protein) to identify compounds that bind to the target molecule (e.g., protein); wherein the concentration of target molecule (e.g., protein) and each compound in each sample is no greater than about 100 $\mu$M. Preferably, the mixture of compounds comprises at least about 3 compounds (more preferably, at least about 6 compounds, and most preferably, at least about 10 compounds), each having at least one distinguishable resonance in an NMR spectrum (preferably, a 1D NMR spectrum, and more preferably, a 1D $^1$H NMR spectrum) of the mixture.

Preferably, in this method, the ratio of target molecule (e.g., protein) to compounds in each sample reservoir is about 1:1. More preferably, the concentration of target molecule (e.g., protein) and each compound in each sample is at least about 25 $\mu$M. Most preferably, the concentration of target molecule (e.g., protein) and each compound in each sample is no greater than about 50 $\mu$M.

Sample requirements can be reduced even further if WaterLOGSY (water-ligand observation with gradient spectroscopy) methods are used as an alternative to the relaxation-editing method described above to detect the binding interaction.

The present invention provides yet another method of identifying a compound that binds to a target molecule (e.g., protein). This method includes: providing a plurality of mixtures of test compounds, each mixture being in a sample reservoir; introducing a target molecule into each of the sample reservoirs to provide a plurality of test samples; providing a nuclear magnetic resonance spectrometer equipped with a flow-injection probe; transferring each test sample from the sample reservoir into the flow-injection probe; collecting a WaterLOGSY nuclear magnetic resonance spectrum (preferably, a 1D WaterLOGSY nuclear magnetic resonance spectrum) on each sample in each reservoir; and analyzing the spectra of each sample to distinguish binding compounds from nonbinding compounds by virtue of the opposite sign of their water-ligand nuclear Overhauser effects (NOEs). Preferably, the concentration of each compound in each sample is no greater than about 100 $\mu$M, although higher concentrations can be used if desired.

In this method when binding is detected using the WaterLOGSY technique, extremely low levels of target can be used with ratios of ligand to target of about 100:1 to about 10:1. Preferably, the concentration of target molecule is no greater than about 10 $\mu$M. More preferably, the concentration of target molecule is about 1 $\mu$M to about 10 $\mu$M. For data analysis, binding compounds are distinguished from nonbinders (i.e., nonbinding compounds) by the opposite sign of their water-ligand NOEs. With this method, there is no need to collect a reference spectrum in the absence of a target molecule.

In preferred embodiments of the present invention, a majority of the compounds in the library have a solubility in deuterated water of at least about 1 mM at room temperature (i.e., about 25° C. to about 30° C.), and a molecular weight of no greater than about 350 grams/mole. For effective use of a compound identified as a ligand for a given target in the search for a lead chemical template, preferably, the dissociation constant of the identified ligand to a target molecule is no weaker than (i.e., at least) about 100 $\mu$M. For effective use of a lead chemical template in further drug design, preferably, the dissociation constant for the lead chemical template to a target molecule is no weaker than (i.e., at least) about 1 $\mu$M.

In another aspect, the invention provides a method of identifying a protein function. The method includes providing a plurality of mixtures of test compounds, each mixture being in a sample reservoir and containing a plurality of test compounds; introducing a target molecule into each of the sample reservoirs to provide a plurality of test samples; providing a nuclear magnetic resonance spectrometer equipped with a flow-injection probe; transferring each test sample from the sample reservoir into the flow-injection probe; collecting a relaxation-edited nuclear magnetic resonance spectrum on each sample in each reservoir; comparing the spectra of each sample to the spectra taken under the same conditions in the absence of the target molecule to identify compounds that bind to the target molecule, wherein the concentration of target molecule and each compound in each sample is no greater than about 100 $\mu$M; and determining a function of the target molecule based upon known binding characteristics of the test compounds that bind to the target molecule.

BRIEF DESCRIPTION OF THE DRAWINGS

FIG. 3A. One-dimensional relaxation-edited $^1$H NMR spectrum of a compound set containing three compounds designated (1), (2), and (3). Resonances are numbered corresponding to the individual components in the set.

FIG. 3B. One-dimensional relaxation-edited $^1$H NMR spectrum of the same set of compounds shown in FIG. 3A in the presence of flavodoxin. Arrows identify resonances that experience a significant reduction in intensity.

FIG. 8A. One-dimensional relaxation-edited $^1H$ NMR spectrum of a compound set containing ten compounds.

FIG. 8B. One-dimensional relaxation-edited $^1H$ NMR spectrum of the same set of compounds in FIG. 8A in the presence of the antiviral target protein. Arrows identify resonances, all belonging to the same compound, that experience a significant reduction in intensity in the presence of the antiviral target protein.

The spectra were recorded at Te=17° C. with 1024 scans and with 2.6 s relaxation delay. The mixing and spin-lock times were 2 and 0.3 s, respectively. The signal at 4.06 ppm, labeled with an asterisk, originates from an exchangeable proton resonance.

Figure 21:
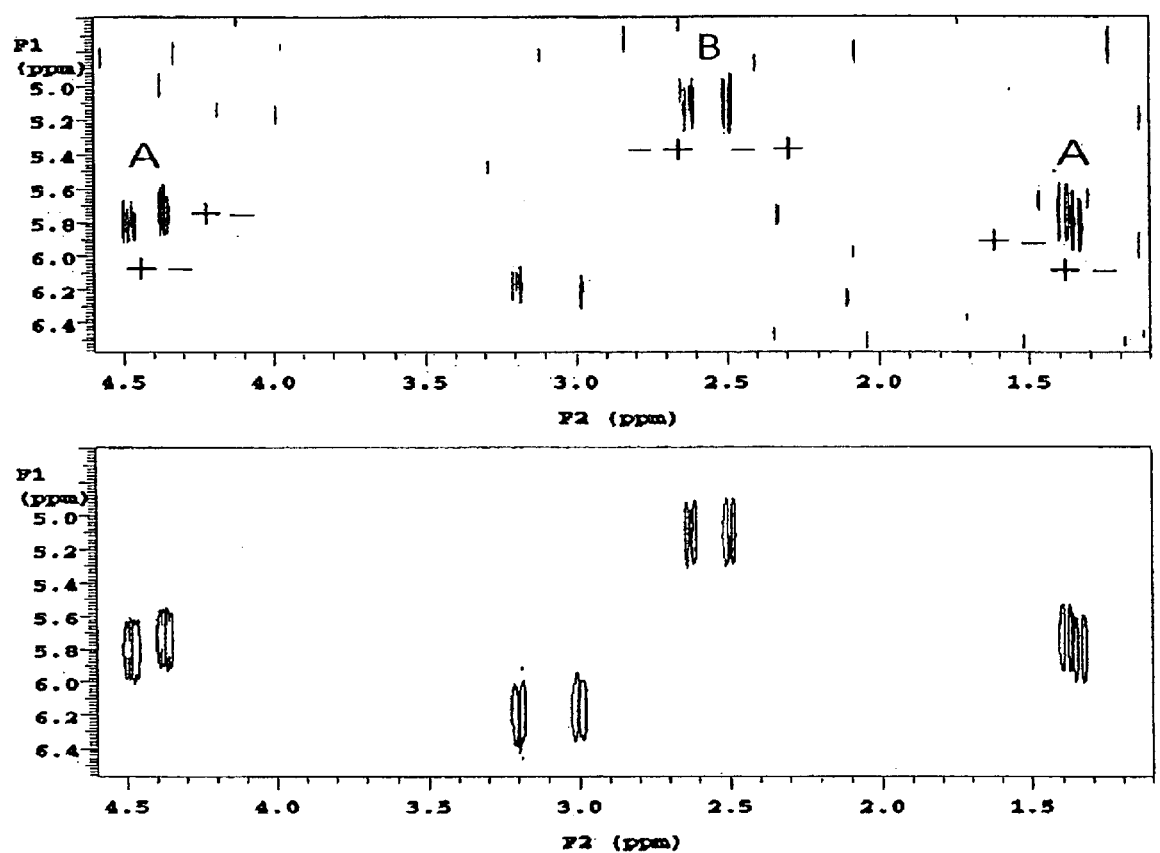

FIG. 21. Expanded region of the WaterLOGSY $^1H$ 2D PFG DQ spectra of the 10compound mixture with cdk2. The spectra above and below were obtained respectively by subtracting and adding the two spectra recorded with $H_2O$ and an off-resonance presaturation rf field of 40 Hz and length 2 s. The 45°/135° version of the experiment was recorded at Te=19° excitation DQ period was 41 ms long and 16 scans were recorded for each of the 128 $t_1$ increments. In the difference spectrum the cross peaks of the two $CH_3$–$CH_2$ moieties (labeled A) of the cdk2 ligand ethyl alpha-(ethoxycarbonyl)-3-indoleacrylate have opposite sign when compared to the cross peaks of the $CH_2$—$CH_2$ moiety (labeled B) of mono-methyl succinate.

DETAILED DESCRIPTION OF PREFERRED EMBODIMENT OF THE INVENTION

The present invention involves the selection of a generally small library of structurally diverse compounds that are generally water soluble, have a relatively low molecular weight, and are amenable to synthetic chemistry elaboration. Significantly and advantageously, for certain embodiments, the present invention preferably involves carrying out a binding assay at relatively low concentrations of target and near equimolar ratios of ligand to target, or even at extremely low concentrations of target and higher ratios of ligand to target.

Figure 1:
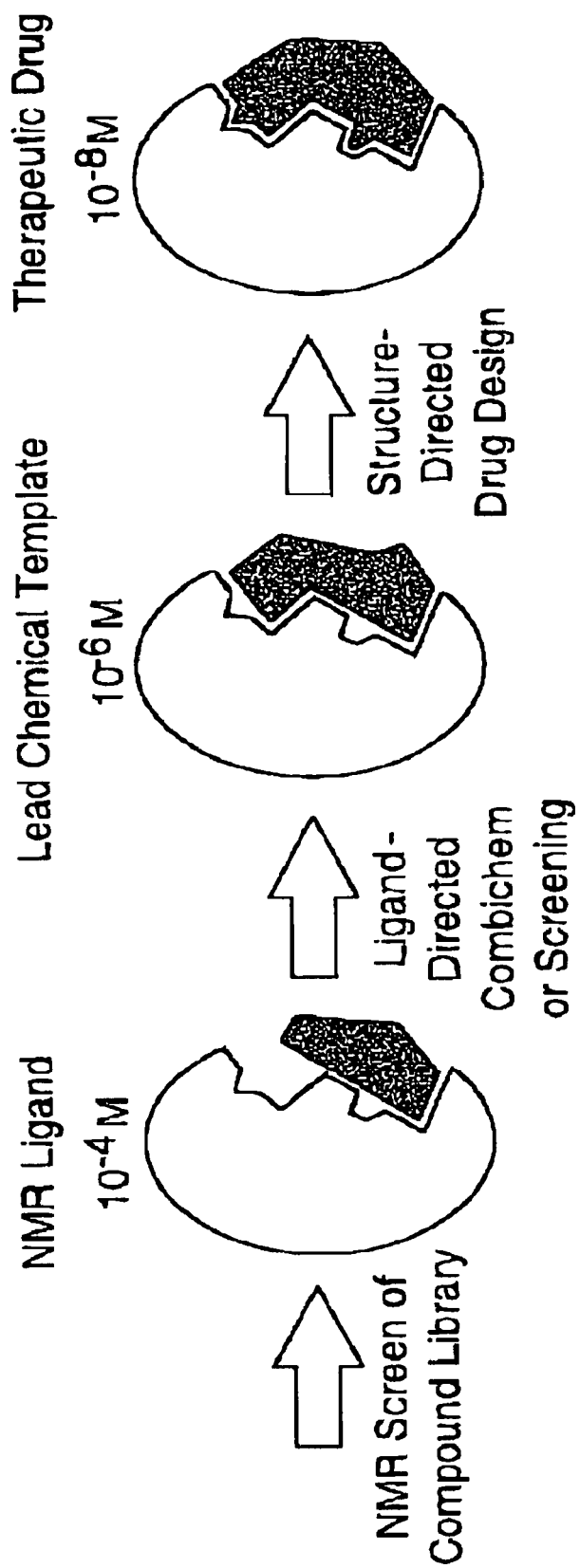
FIG. 1. Schematic diagram illustrating the use of NMR to discover a ligand having an approximate dissociation constant of $1.0 \times 10^{-4}$ M (left figure), to use the discovered ligand to direct the discovery of a lead chemical template having an approximate dissociation constant of $1.0 \times 10^{-6}$ M (middle figure), and then via synthetic chemistry and structure-directed drug design arrive at a drug candidate having an approximate dissociation constant of $1.0 \times 10^{-8}$ M.

In a method of the present invention, a relatively small subset of compounds (preferably, at least about 75, more preferably, at least about 300, most preferably, at least about 2000, and typically no more than about 10,000) that mimics the structural diversity of compounds in much larger collections is created based on a predetermined set of criteria. This generally small library is screened for binding affinity to a target molecule (as determined herein by dissociation constants). The compounds from the library that are identified to be effective ligands (typically, having an affinity for a desired target as evidenced by a dissociation constant of at least about $1.0 \times 10^{-4}$ M) are then used to focus further screening efforts or to direct chemical elaborations to arrive at one or more lead chemical templates (which, typically have an affinity for a desired target as evidenced by a dissociation constant of at least about $1.0 \times 10^{-6}$ M). This process is shown schematically in FIG. 1.

Significantly, time and resources are saved by screening far fewer compounds using the present invention. Use of a binding assay, such as the one based on NMR spectroscopy described herein, eliminates the need to develop a high-throughput functional assay, and also allows the methods to be used on molecular targets lacking a known function.

Thus, the present invention provides methods of identifying a compound that binds to a target molecule (preferably, a protein) that are based on NMR spectroscopy techniques. Such methods typically involve the use of relaxation-editing techniques, for example, which involve monitoring changes in resonance intensities (preferably, significant reductions in intensities) of the test compound upon the addition of a target molecule. Preferably, the relaxation-editing techniques are one-dimensional, and more preferably, one-dimensional $^1$H NMR techniques. Alternatively, such methods can involve the use of Water-LOGSY. This involves the transfer of magnetization from bulk water to detect the binding interaction. Using Water-LOGSY techniques, binding compounds are distinguished from nonbinders by the opposite sign of their water-ligand nuclear Overhauser effects (NOEs).

Important elements that contribute to the success of the methods of the invention preferably include developing a suitable small library of compounds to screen, carrying out the binding assay at low concentrations of target and near equimolar ratios of ligand to target (for relaxation-editing), or at extremely low concentrations of target (if desired) and higher ratios of ligand to target (for WaterLOGSY), and the capacity for rapid throughput of data collection. For example, for relaxation-editing NMR techniques, the concentration of target molecule is preferably no greater than about $1.0 \times 10^{-4}$ M, and for WaterLOGSY NMR techniques, the concentration of target molecule is preferably no greater than about 10 $\mu$M.

The selection of compounds in a small library (preferably, at least about 75 compounds, more preferably, at least about 300 compounds, and most preferably, at least about 2000 compounds) is important in that its diversity should mimic the diversity of larger compound collections. Preferably, each component possesses many of the desirable qualities of a lead chemical template. These include water solubility, low molecular weight (preferably, no greater than about 350 grams/mole, more preferably, no greater than about 325 grams/mole, and most preferably, less than about 325 grams/mole), and amenability to synthetic chemistry elaboration. Templates possessing these qualities, as compared to a template selected randomly, are preferably considered to be predisposed to being lead-like and having an increased likelihood of ultimately leading to a drug.

Good structural diversity in a library increases the likelihood that one or more compounds will possess structural characteristics important for binding to a given molecular target. Predisposing the compounds to be water soluble, to have low molecular weight (preferably, no greater than about 350 grams/mole, more preferably, no greater than about 325 grams/mole, and most preferably, less than about 325 grams/mole), and to be amenable to synthetic elaboration increases the likelihood that a compound found to be a ligand will lead to a related compound or compounds suitable as a lead chemical template for use, for example, in a process of identifying an effective therapuetic and/or prophylactic agent. Additionally, the requirement for good water solubility (preferably, at least about $1.0 \times 10^{-3}$ M in deuterated water at room temperature) is important in that it increases the likelihood of success of other downstream drug-design projects, such as co-crystallization attempts, calorimetry studies, and enzyme kinetic analyses.

Carrying out a relaxation-editing binding assay (preferably, a 1D $^1$H NMR assay) at low concentrations of target (preferably, no greater than about $1.0 \times 10^{-4}$ M, and more preferably, no greater than about $5.0 \times 10^{-5}$ M) and near equimolar ratios of ligand to target creates the requirement that compounds testing positive for binding have affinities within a factor of about 3–4 of this same concentration (preferably, having a dissociation constant of no less than about $2.0 \times 10^{-4}$ M). A similar affinity threshold can be obtained by carrying out a WaterLOGSY based binding assay at even lower target concentrations (preferably, no greater than about 10 $\mu$M, but is more preferably about 1 $\mu$M to about 10 $\mu$M) and ligand to target ratios of about 100:1 to about 10:1. This level of affinity is desired if the subsequent steps of focused screening and directed chemical elaboration are to be successful in elucidating a lead chemical template with very low affinity (e.g., one having a dissociation constant of at least about $1.0 \times 10^{-6}$ M). Carrying out the initial screening at these low concentrations also avoids detection of unwanted compounds with much smaller dissociation constants in the $1.0 \times 10^{-3}$ M range, which are less specific in their binding and therefore harder to turn into lead chemical templates given their weak affinity initially.

The capacity for rapid throughput of data collection is important if a large number of molecular targets are to be screened. Preferably, flow NMR techniques can reduce the amount of time and effort required to evaluate small molecules for binding to a given target. For example, the use of a Bruker Efficient Sample Transfer system in combination with a tubeless, flow-injection NMR probe has proven to be much faster and less labor intensive than the use of traditional NMR tubes. A significant increase in throughput is obtained compared to both manual sample changing and to using an autosampler. Implementation of the screening process using multiwell sample holders also standardizes the experimental setup as well as the components in a given mixture from one molecular target to the next.

The following is a description of a preferred method for carrying out the present invention. It is provided for exemplification purposes only and should not be considered to unnecessarily limit the invention as set forth in the claims.

Figure 2:
FIG. 2. Comparison of the two-dimensional HA (hydrogen-bond acceptor) vs. CHRG (charge) BCUT plots for the compounds contained in the NMR library described herein (dark squares) and a larger chemical library database (gray spots).

In the design of a preferred small library of structurally diverse compounds according to the present invention, compounds were selected from a large library based on dissimilarity, predicted water solubility, low molecular weight, and chemical intuition. Some were based on frameworks suggested in the literature, although some literature-suggested frameworks were consciously avoided. Each compound was tested for solubility at $1.0\times10^{-3}$ M in $^2H_2O$ and for purity by mass spectrometry and $^1H$ NMR spectroscopy. Compounds deemed to be water soluble and pure were kept for inclusion in the final library (approximately 30% of the initial compounds). The resulting library contains approximately 300 compounds. One measure of the degree of structural diversity of the compounds in this small library is shown in FIG. 2. This is based on the technique described in Pearlman et al., *Perspectives in Drug Discovery & Design*, 9, 339–353 (1998). Preferably, the compound library includes compounds of sufficiently diverse chemical structure that one would expect at least one compound to bind to a given target protein with an affinity (dissociation constant) no weaker than (i.e., at least) about 200 µM. Herein, compounds of diverse chemical structure are those that have a variety of backbone hydrocarbon structures (e.g., linear, branched, cyclic—which may or may not be aromatic, have fused rings, etc.), optionally including a variety of heteroatoms (e.g., oxygen, nitrogen) and a variety of functional groups (e.g., carbonyls) in a variety of positions (e.g., pointing in various directions at a variety of distances from each other). Ideally, using the technique described in Pearlman et al., *Perspectives in Drug Discovery & Design*, 9, 339–353 (1998), the library of compounds displays a pattern of well-dispersed black squares (e.g., see FIG. 2).

In order to increase the throughput of the NMR screening, compounds were grouped into 32 sets of 6–10 compounds that have at least one distinguishable resonance in a 1D $^1H$ NMR spectrum of the mixture. To accomplish this, a 1D $^1H$ NMR spectrum was obtained of each mixture in 100% $^2H_2O$ and in 0.1 M sodium phosphate/100% $^2H_2O$ at pH 6.5. Two solvents were used in order to determine the assignment of pH-titratable resonances in the spectrum. Each of the 32 mixtures was then plated out into separate wells of a 96-well plate, using 25 µL of a $1.0\times10^{-3}$ M solution, and frozen at $-80°$ C. until needed. In an initial version of the NMR screening library, approximately 70 compounds were grouped into 21 sets of 3–4 compounds each.

After a 96-well plate had completely thawed, a solution containing a molecular target protein was added to each well containing a mixture of compounds in the 96-well plate. The final concentration of protein is typically about $5.0\times10^{-5}$ M. The ratio of each compound in a mixture to protein is typically about 1:1. This process typically involves adding 475 mL of protein to each mixture. Dispersion throughout the mixture was facilitated by shaking the 96-well plate for 20 minutes following addition of protein.

A 1D relaxation-edited $^1H$ NMR spectrum was collected on each protein/compound mixture solution using a Bruker DRX600 or a Bruker AMX400 spectrometer equipped with a shielded magnet, a Gilson sample handler, and a 5 mm (250 µL sample cell) flow-injection NMR probe. The use of a shielded magnet greatly reduces the magnetic fringe field surrounding the high field magnet and allows the Gilson sample handler to be placed in close proximity to the magnet. The Gilson liquid sample handler transfers samples from 96-well plates into the flow-injection probe and, if desired, returns the samples back to the 96-well plate. A compound or compounds that bind to a given target are identified by comparing the 1D relaxation-edited $^1H$ NMR spectrum collected in the presence of added protein to that of the identical mixture of compounds in the absence of protein. A compound is identified as a ligand for a given target if one or more of its resonances (preferably $^1H$ resonance or resonances) are significantly reduced (i.e., greater than about 75% reduction in one or more resonances) in intensity in the presence of target molecule (e.g., protein) as compared to the spectrum collected in an identical fashion in the absence of target molecule (e.g., protein).

Sample requirements can be reduced even further if WaterLOGSY methods are used as an alternative to the relaxation-editing method described above to detect the binding interaction. WaterLOGSY is described in more detail in C. Dalvit et al., *J. Biomol.* NMR, 18, 65–68 (2000).

Water plays a pivotal role in the protein-ligand, protein-protein and protein-DNA recognition mechanisms. Based on numerous observations in this regard (Otting, *Progr. NMR Spectrosc.*, 31:259–285 (1997): Dalvitet al., *J. Biomol. NMR*, 13:43–50 (1999): Otting et a)., *Science.* 254(5034): 974–980 (1991): Otting et al., *J. Am. Chem. Soc.* 111:1871–1875 (1989); and Kallen et al., *J. Mol. Biol.*, 292:1–9 (1999)), $H_2O$ can be used for the detection of molecules interacting with a protein. Two different classes of experiments can be used for this purpose, i.e., a steady state NOE experiment with on-resonance saturation applied at the water chemical shift or a NOE experiment with selective inversion of the $H_2O$ signal and with a long mixing time. Numerous schemes have been devised for selective water excitation (Otting, *Progr. NMR Spectrosc.*, 31:259–285 (1997) and references therein). A member of this type of experiments is the NOE-ePHOGSY and related experiments (Dalvit et al., *J. Magn. Reson. B.*, 109:334–338 (1995): Dalvit, *J. Magn. Reson. B.* 112(3):282–288 (1996): Melacini et al., *J. Biomol., NMR.* 13:67–71 (1999a): Melacini et al., J Biomol. NMR, 15:189–201 (1999b).

The saturation of water yields the following effects: (i) saturation of some of the αH protein resonances, (ii) complete saturation of the fast exchanging NH and OH protons of the protein and small molecules resonating at the $H_2O$ chemical shift, (iii) partial or total saturation of rapidly exchanging NH and OH protons of the protein and small molecules resonating at a chemical shift different from $H_2O$, (iv) magnetization transfer from bulk water to bound water located in different cavities of the protein, and (v) magnetization transfer from bulk water to the squeezed water at the protein-ligand interface. Inversion of most of this magnetization is achieved in the NOE-ePHOGSY experiment with the exception, in large biomolecules, of the αH protein signals resonating at the $H_2O$ chemical shift (i). The acquisition of these experiments is technically demanding when working in $H_2O$. Often the effects observed in the difference spectra are very small. Radiation damping and demagnetizing field mechanisms originating from bulk water can introduce artifacts and mask the small effects (Sobol et al., *J. Magn Reson.*, 130(2):262–271 (1998): Price, *Annual Reports on NMR Spectroscopy* (Ed., Webb. A.), Academic Press, New York., vol. 38, pp. 289–354 (1999)). However, it is possible to overcome these problems by properly using pulsed field gradients.

Figure 18:
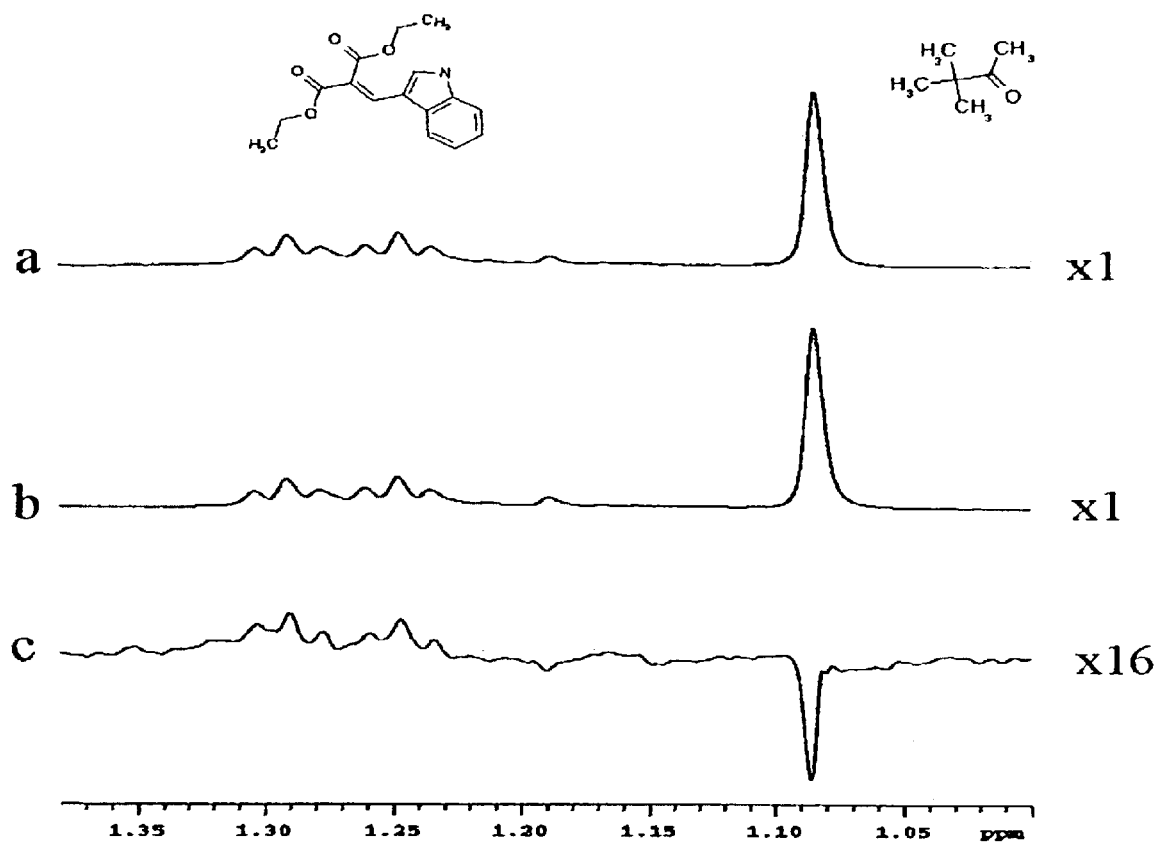
FIG. 18. Expanded region of the 1D $^1H$ WaterLOGSY spectrum of a 10 compound mixture (see text) in the presence of the protein cdk2 recorded with a 40 Hz and 2 s long RF presaturation field applied off-resonance (a) and at the $H_2O$ chemical shift (b). (c) Difference spectrum obtained by subtracting spectrum (b) from spectrum (a). Human cdk2 protein was expressed in Sf9 insect cells using a recombinant baculovirus encoding cdk2. The NMR sample was in Phosphate Buffered Saline (PBS) (8% $D_2O$) and the protein concentration was 10 $\mu$m. The spectra Have been recorded at Te=19° C. with a Varian Inova 600 MHz spectrometer. The $H_2O$ solvent suppression was achieved with the $H_2O$ excitation sculpting sequence (Hwang et al., J. Magn. Reson. A112:275–279(1995). A total of 256 scans were recorded for each spectrum (a,b). The chemical structures of the two molecules are depicted. Positive and negative signals in (c) identify cdk2 interacting and not interacting molecules, respectively.

WaterLOGSY (Water-Ligand Observation with Gradient Spectroscopy) is the term applied for these experiments used for detection of ligands via bulk water. FIG. 18 shows the principle of the experiment recorded with steady state NOE applied to a mixture of 10 low molecular weight compounds (concentration 100 µm) in the presence of 10 µm of cyclin-dependent kinase 2 (cdk2) protein (Mw ~34 kDa). The molecules of the mixture are 3-methylenecyclopropane-trans-1,2-dicarboxylic acid, mono-methyl succinate, s-benzylthioglycolic acid, 3,3-dimethylacrylic acid, 1,2,4-triazole, 5,5-dimethyl-2-4-oxazolidinedione, 2,2-dimethyl-1,3-dioxane-4,6-dione, fluoroacetamide, pinacolone and ethyl alpha-(ethoxycarbonyl)-3-indoleacrylate. The expanded region contains only the two methyl group signals (1.29 and 1.25 ppm) of the indole derivative and the methyl t-butyl signal (1.08 ppm) of pinacolone. The spectra in (a) and (b) were recorded with water and off-resonance saturation, respectively. A weak positive NOE effect (negative signal) for pinacolone and a weak negative NOE effect (positive signals) for the indole derivative are observed in the difference spectrum (FIG. 18c). Pinacolone does not interact with the protein and therefore displays a positive NOE with $H_2O$ whereas the indole derivative that interacts with the protein (measured Ki is in the high urn range) displays a negative NOE stemming from the effects associated to the saturation of bulk $H_2O$, as described above.

Figure 19:
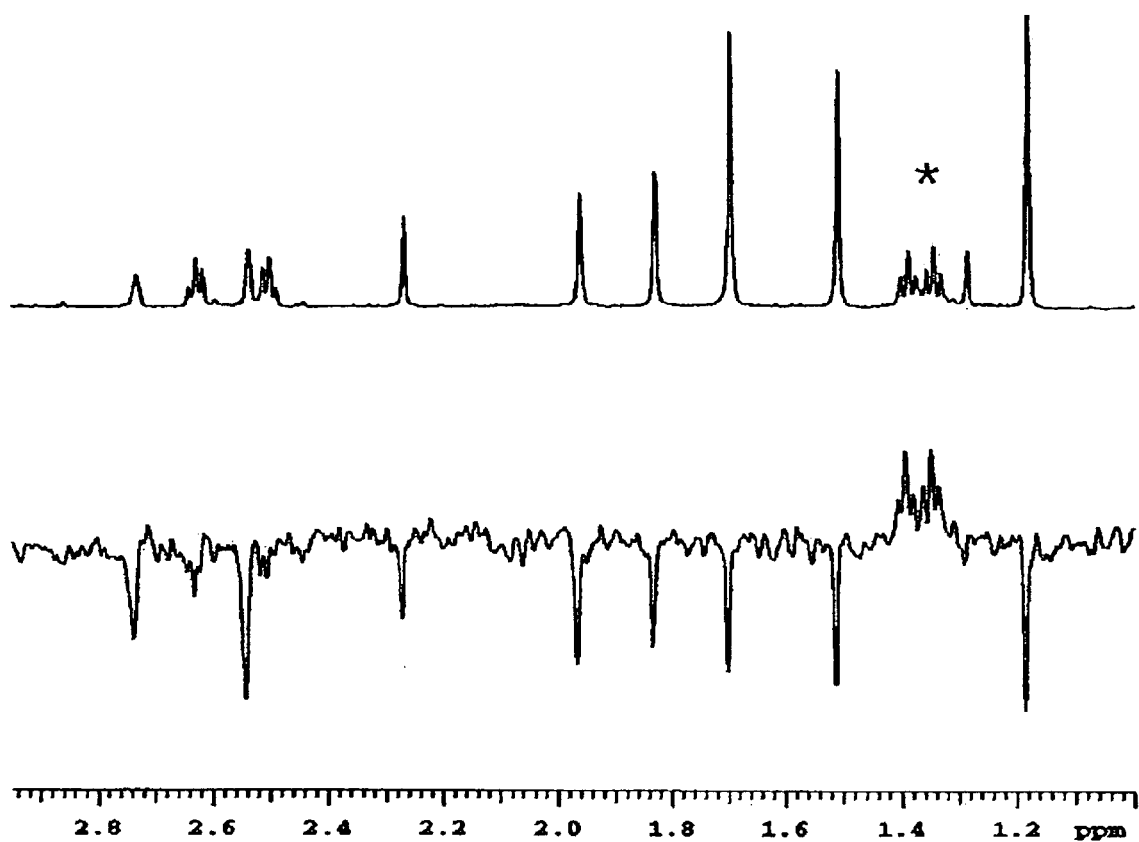
FIG. 19. One-dimensional reference (upper) and Water-LOGSY with NOE-ePHOGSY (lower) spectra recorded for the 10-compound chemical mixture in the presence of 10 $\mu$m cdk2. The WaterLOGSY and the reference spectra were recorded at Te=17° C. with 256 and 128 scans, respectively. The $H_2O$ solvent suppression in both experiments was achieved with the $H_2O$ excitation sculpting sequence (Hwang et el., J. Magn. Reson. A112:275–279(1995). The WaterLOGSY was recorded with a 38 ms long 180° $H_2O$ selective Gaussian pulse. This pulse can be set also to only 10 to 20 ms length, because no high selectivity is required. The relaxation and mixing times were 2.6 and 2 s, respectively. Positive and negative signals in the lower spectrum identify cdk2 interacting and not interacting molecules, respectively. The asterisk indicates the methyl group resonances of the cdk2 ligand ethyl alpha-(ethoxycarbonyl)-3indoleacrylate.
Figure 20:
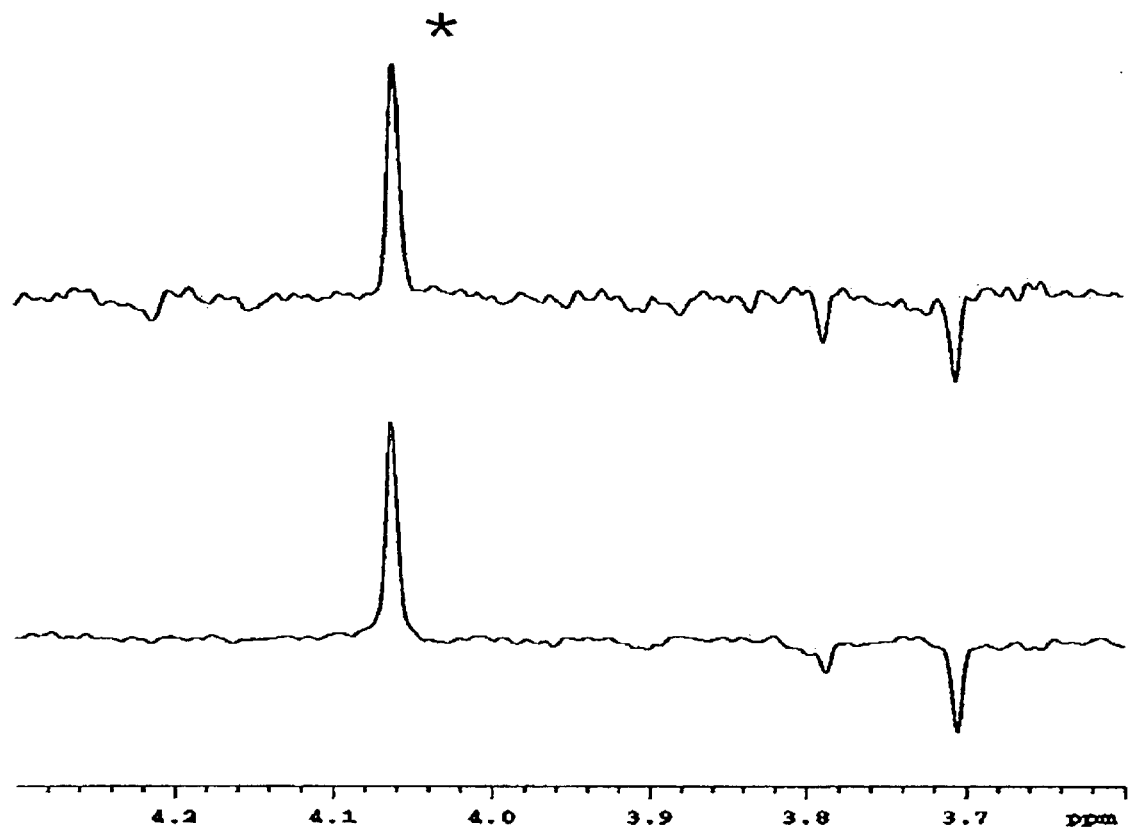
FIG. 20. Expanded region of 1D WaterLOGSY with NOE-ePHOGSY (lower) and ROE-ePHOGSY (upper) spectra for the 10compound mixture in the presence of 10 $\mu$m cdk2.

The 1D WaterLOGSY experiments with the $H_2O$ presaturation scheme can give rise to small artifacts originating from the difference spectroscopy method. However, the version with the NOE-ePHOGSY scheme is completely devoid of artifacts. Even very weak effects can be analyzed with confidence. This can be appreciated in FIG. 19. The 10 small molecules mixture contains NMR signals consisting mostly of sharp singlets. Comparison of the 1D NOE-ePHOGSY (lower spectrum) with the 1D reference spectrum (upper spectrum) allows easy identification of the only molecule interacting with the protein. The measuring time of the WaterLOGSY spectrum of FIG. 19 was only 20 min. The quality of the spectra obtainable with the NOE-ePHOGSY scheme and the sensitivity of the experiment have allowed application of the method to protein concentrations as low as a few hundred nM (data not shown). The exchangeable proton resonances, when visible, will also appear as positive peaks in the WaterLOGSY experiments. These peaks usually can be easily recognized in the spectrum. However, if doubts remain it is sufficient to record the WaterLOGSY experiment with the ROE-ePHOGSY scheme for the unambiguous identification of the exchangeable resonances. FIG. 20 shows application of this strategy. The positive peak at 4.06 ppm observed in the WaterLOGSY with NOE step (lower spectrum) does not originate from a ligand of cdk2, but it is simply an exchangeable proton resonance as confirmed by the WaterLOGSY experiment with ROE step (upper spectrum).

The WaterLOGSY schemes (either with $H_2O$ presaturation or NOE-ePHOGSY) can be also used in 2D experiments (DQ, TOCSY, etc.). Use of Water-LOGSY in the $^1H$ 2D PFG DQ experiment applied to our compound mixture is shown in FIG. 21. The signals of the $CH_3-CH_2$ moiety of the cdk2 ligand ethyl alpha-(ethoxycarbonyl)-3-indoleacrylate and the signals of the $CH_2-CH_2$ moiety of mono methyl succinate are visible in this expanded spectral region (lower spectrum). These signals are also visible in the DQ difference spectrum (upper spectrum). However, the signals of the ligand are easily recognized because they have opposite sign when compared to the signals of mono methyl succinate.

Thus, it is possible to use the large reservoir of bulk $H_2O$ magnetization to detect via different transfer mechanisms small molecules that interact with a target biomolecule (proteins, DNA or RNA fragments). The method, like all the techniques based on ligand resonance observation, has the disadvantage that it does not provide information about the ligand binding site. Despite this drawback the technique represents a rapid means for ligand identification.

Since the WaterLOGSY experiment relies on the transfer of magnetization from bulk water to detect the binding interaction, it is a very sensitive technique. As such, the concentration of target molecule (e.g., protein) in each sample preferably can be reduced to no greater than about 10 $\mu M$ (preferably, about 1 $\mu M$ to about 10 $\mu M$) while the concentration of each compound can be about 100 $\mu M$. This results in ratios of test compound to target molecule in each sample reservoir of about 100:1 to about 10:1. The exact concentrations and ratios used can vary depending on the size of the target molecule, the amount of target molecule available, the desired binding affinity detection limit, and the desired speed of data collection. In contrast to the relaxation-editing method, there is no need to collect a comparison or control spectrum to identify binding compounds from non-binders. Instead, binding compounds are distinguished from nonbinders by the opposite sign of their water-ligand nuclear Overhauser effects (NOEs).

Ligand binding was confirmed by making fresh solutions containing only the identified ligand, with and without added protein at a 1:1 ratio, and comparing the 1D relaxation-edited $^1H$ NMR spectra. In addition, the ligand's dissociation constant was estimated by analyzing several 1D diffusion-edited 1H NMR spectra collected at several gradient strengths. The relative diffusion coefficients for the protein, for the ligand in the presence of protein, and for the ligand in the absence of protein, in conjunction with known protein and ligand concentrations, were used to estimate the ligand's dissociation constant. These spectra are typically collected using an NMR spectrometer, a conventional high resolution probe, and regular 5 mm NMR tubes.

Once a ligand had been identified and confirmed, its structure is used to identify available compounds with similar structures to be assayed for activity or affinity, or to direct the synthesis of structurally related compounds to be assayed for activity or affinity. These compounds are then either obtained from inventory or synthesized. Most often, they are then assayed for activity using enzyme assays. In the case of molecular targets that are not enzymes or that do not have an enzyme assay available, these compounds can be assayed for affinity using NMR techniques similar to those described above, or by other physical methods such as isothermal denaturation calorimetry. Compounds identified in this step with affinities for the molecular target of about $1.0 \times 10^{-6}$ M are typically considered lead chemical templates.

In some instances, ligand binding is further studied using more complex NMR experiments or other physical methods such as calorimetry or X-ray crystallography. These downstream studies have a greater chance of success since the ligands and lead chemical templates so identified are fairly water soluble. For instance, if [$^{15}N$]protein is available, $2D^1H-^{15}N$ HSQC (heteronuclear single quantum correlation) spectra can be collected with and without added ligand to locate the ligand's binding site on the protein. In cases where the protein is small enough (molecular weight less than about 30,000) and further characterization of protein/ligand interactions is desired, 3D NMR experiments can be carried out on [$^{13}C/^{15}N$]protein/[$^{12}C/^{14}N$]ligand complexes. Attempts to soak lead chemical templates identified by this method into existing protein crystals, or to form co-crystals, can also be carried out.

EXAMPLES

Objects and advantages of this invention are further illustrated by the following examples, but the particular materials and amounts thereof recited in these examples, as well as other conditions and details, should not be construed to unduly limit this invention.

Example 1

Use of NMR Spectroscopy to Identify Ligands for Flavodoxin

Reference 1D $^1$H NMR spectra of the individual compounds and combinations of compounds were recorded in $^2$H$_2$O solution on a Bruker ARX-400 spectrometer. One-dimensional relaxation-edited $^1$H NMR spectra of samples containing a mixture of flavodoxin and a given compound combination were recorded in $^2$H$_2$O solution on a Bruker DRX-500 spectrometer. A spin lock time of 350 milliseconds was used. The screening experiments were carried out on solutions that were 5.0×10$^{-5}$ M flavodoxin and 1.0×10$^{-4}$ M of each ligand present. Two-dimensional $^1$H-$^{15}$N HSQC spectra were recorded in $^1$H$_2$O solution on a Bruker DRX-500 spectrometer. Samples were 5.0×10$^{-5}$ M flavodoxin with a 3–10 fold excess of a given ligand. All solutions containing flavodoxin were buffered with 1.0×10$^{-2}$ M phosphate at pH 6.4. The *Desulfovibrio vulgaris* flavodoxin used in all experiments was $^{15}$N-enriched.

To create the NMR ligand screening library, an initial set of compounds was selected by a search of a larger library of compounds based on dissimilarity, predicted water solubility, low molecular weight (preferably, no greater than about 350 grams/mole, more preferably, no greater than about 325 grams/mole, and most preferably, less than about 325 grams/mole), and chemical intuition. These compounds were then tested for water solubility and purity. Compounds with no visible precipitate or suspension at a concentration of 1.0×10$^{-3}$ M were deemed to be water soluble. Compounds with the predicted parent ion molecular weight and otherwise normal mass spectra were deemed to be pure. Reference 1D $^1$H NMR spectra were collected on compounds meeting these criteria. Combinations of three or four compounds were then assembled in which at least one distinguishing $^1$H NMR resonance for each compound could be readily identified. A reference 1D $^1$H NMR spectrum was then recorded for each combination of compounds. As an example, three compounds, designated here as (1), (2), and (3), were combined into one set. The 1D $^1$H NMR spectrum of this combination set is illustrated in FIG. 3A. Resonances from each of the individual components are readily identified, especially in the aliphatic region of the spectrum. At the time of this work, the NMR ligand library contained approximately 70 compounds incorporated into 21 unique assortments containing three or four compounds each.

One-dimensional relaxation-edited $^1$H NMR spectroscopy was used to screen the library for binding to the model target protein, *Desulfovibrio vulgaris* flavodoxin. For most of the compound combinations in the presence of flavodoxin, there was little or no reduction in resonance intensity with the 350-millisecond spin-lock time. However, for two of the compound combinations, the intensities of resonances corresponding to one of the compounds in the mixture were significantly reduced. FIG. 3B exemplifies this for the same combination illustrated in FIG. 3A. The resonances corresponding to (2) and (3) are not affected by the spin-lock filter in the presence of flavodoxin. However, the two aliphatic resonances of (1) at 1.8 ppm and 3.7 ppm are significantly reduced in intensity by the spin-lock filter in the presence of flavodoxin, indicating that (1) is binding to the protein. Similar experiments indicated that a second compound, contained within a different combination of compounds, also binds to flavodoxin. These were the only two compounds among those tested that clearly bind to flavodoxin.

Figure 4A:
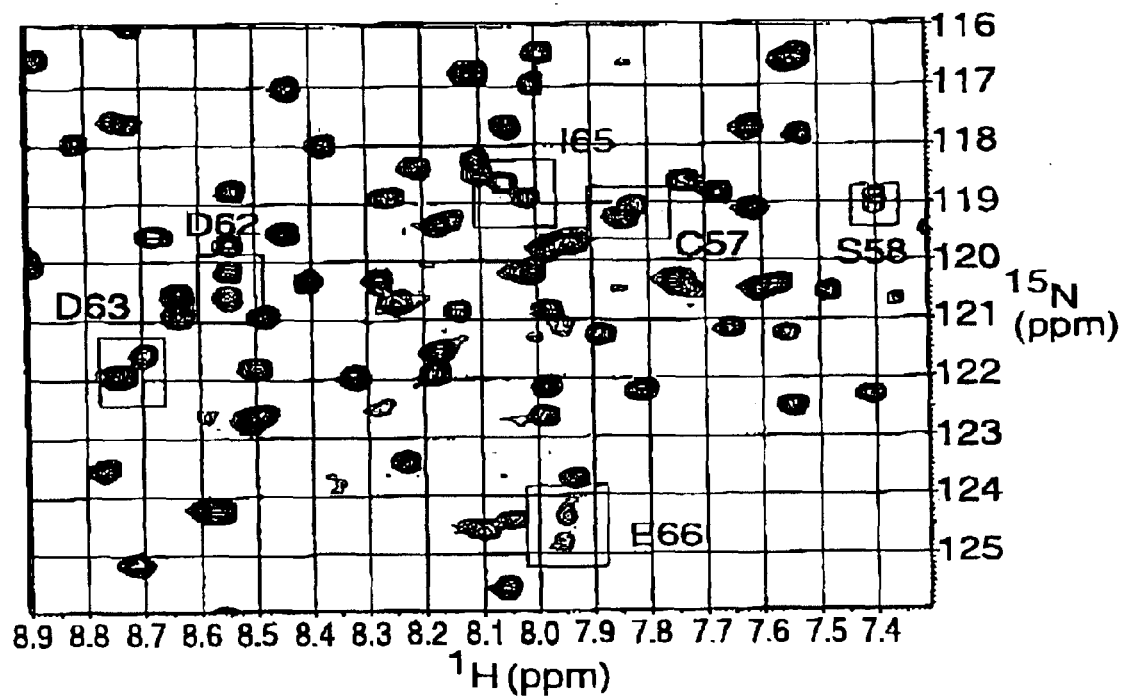
FIG. 4A. Region of the 2D $^1$H-$^{15}$N HSQC spectrum of flavodoxin alone and in the presence of a 10-fold excess of compound (1). Residues with significant chemical shift changes in the presence of (1) are boxed and labeled with their amino acid type and sequence number.
Figure 4B:
FIG. 4B. Secondary structure representation of the flavodoxin global fold. The flavin cofactor is shown in stick format. Residues with the largest chemical shift changes in the presence of (1) are shown in white.

Two-dimensional $^1$H-$^{15}$N HSQC spectra were subsequently recorded on [$^{15}$N]flavodoxin to further investigate the interaction of these two ligands with the protein. Since amide backbone $^1$H and $^{15}$N resonance assignments for this protein are known (Stockman et al., *J. Biomol. NMR*, 3, 133–149 (1993)), analysis of the ligand-induced changes in $^1$H and $^{15}$N chemical shifts could be used to identify the ligand binding sites. Typical chemical shift changes observed are delineated in FIG. 4A, which shows an overlay of the $^1$H-$^{15}$N HSQC spectra of flavodoxin alone and in the presence of excess (1). Residues with the largest ligand-induced chemical shift changes are indicated in white on the structure of the protein (Watt et al., *J. Mol. Biol.*, 218, 195–208 (1991)) in FIG. 4B. Compound (1) binds near the flavin cofactor binding site. Interestingly, the binding sites as defined by this data for the two ligands identified are at adjacent, partially overlapping locations on the surface near the flavin cofactor binding site.

Example 2

Use of NMR Spectroscopy to Identify a Lead Chemical Template for an Antibacterial Target Protein Numerous protein targets are amenable to an NMR process of identifying a lead chemical template. In this example, the technique is illustrated for an antibacterial target protein with a molecular weight of about 20 kDa.

All solutions containing the antibacterial target protein were buffered with 2.5×10$^{-2}$ M phosphate at pH 7.4. The protein used for the 1D screening and dissociation constant determination experiments was unlabeled, while that used for the 2D $^1$H-$^{15}$N HSQC experiments was $^{15}$N-enriched.

One-dimensional relaxation-edited $^1$H NMR spectra of samples containing a mixture of the target protein and a given compound combination were recorded in $^2$H$_2$O solution on a Bruker DRX-500 spectrometer. A spin lock time of 350 milliseconds was used. The screening experiments were carried out on solutions that were 1.0×10$^{-4}$ M target protein and 1.0×10$^{-4}$ M of each ligand. The library used for the screening process was identical to that described in Example 1.

Two-dimensional $^1$H-$^{15}$N HSQC spectra were recorded in $^1$H$_2$O solution on a Bruker DRX-500 spectrometer. Samples contained 8.0×10$^{-5}$ M target protein with a 9–10 fold excess of a given ligand.

Ligand dissociation constants were estimated by determining relative diffusion coefficients for target protein alone, ligand in the absence of target protein, and ligand in the presence of target protein (Lennon et al., *Biophys. J.*, 67, 2096–2109 (1994)). Relative diffusion coefficients were determined using pulsed-field-gradient NMR experiments incorporating a bipolar longitudinal eddy-current delay sequence (Wu, *J. Magn. Reson. Ser. A*, 115, 260–264 (1995)).

One-dimensional relaxation-edited $^1$H NMR spectroscopy was used to screen the small molecule library for binding to this target protein in a manner analogous to that previously described in Example 1. With this technique, a reduction in resonance intensity is observed if a compound interacts with the target protein, thus identifying it as a ligand. For most of the compound combinations in the presence of the antibacterial target protein, there was little or no reduction in resonance intensity with the 350-millisecond spin-lock time. However, for some of the compound combinations, the intensities of resonances corresponding to one of the compounds in the mixture were significantly reduced. The results from one such compound combination are described here.

Figure 5A:
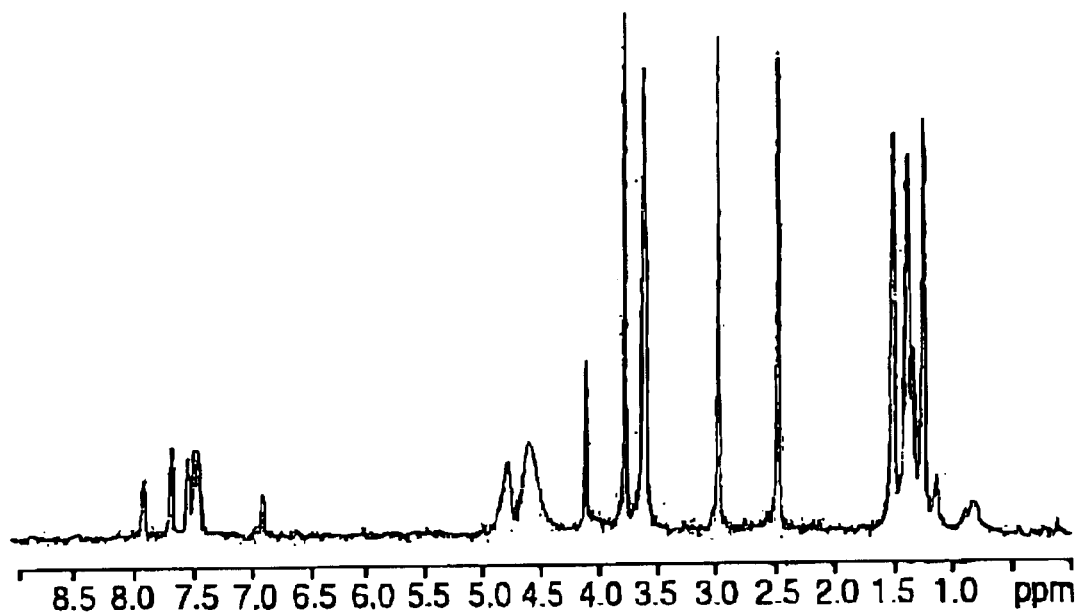
FIG. 5A. One-dimensional relaxation-edited $^1$H NMR spectrum of a compound set containing three compounds in the presence of flavodoxin.
Figure 5B:
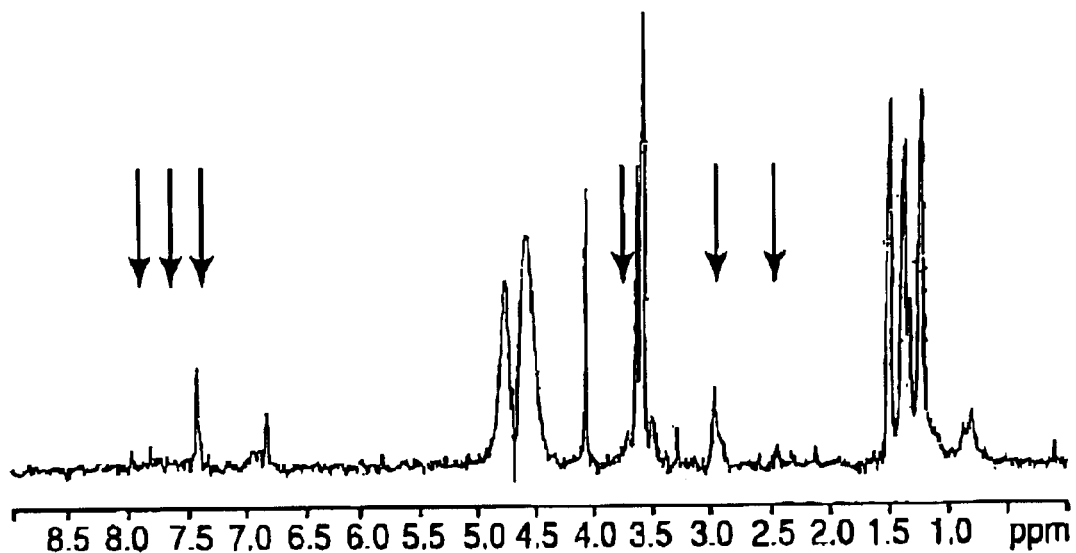
FIG. 5B. One-dimensional relaxation-edited $^1$H NMR spectrum of the same compound set shown in FIG. 5A in the presence of the antibacterial target protein. Arrows identify resonances from Ligand A (FIG. 6) that experience a significant reduction in intensity in the presence of the antibacterial target protein.

As a control, the 1D relaxation-edited $^1$H NMR spectrum of a certain mixture in the presence of a different protein, flavodoxin, is shown in FIG. 5A. All ligand resonances are observed with full intensity. The corresponding 1D relaxation-edited $^1$H NMR spectrum of this same mixture acquired in the presence of the antibacterial target protein is shown in FIG. 5B. The intensities of all resonances corresponding to Ligand A in FIG. 5B are clearly reduced in the presence of the antibacterial target protein. This indicates that Ligand A is binding to the protein. The binding is specific to the antibacterial target protein since the resonance intensities are not reduced in the presence of flavodoxin.

Binding of Ligand A was confirmed by repeating the relaxation-filtered experiments on a solution containing protein and just Ligand A. Using this same sample, as well as samples of protein alone and Ligand A alone, a separate set of experiments that use pulsed-field-gradient techniques was collected to determine relative diffusion coefficients. From this data, the dissociation constant for Ligand A was estimated by NMR measurements to be approximately $1.4 \times 10^{-4}$ M.

In order to ascertain whether the binding of Ligand A and structurally related analogs inhibited the activity of this enzyme, and if so to what degree, $IC_{50}$ values were determined. To determine $IC_{50}$ values, various concentrations of selected compounds, originally prepared at $1.0 \times 10^{-2}$ M in 100% DMSO, were titered out to provide at least 12 individual concentrations. Twenty five (25) µL of each solution (15% DMSO maximum) were added to wells in a 96-well plate, followed by 100 microliters (µL) of a cocktail containing 100 nanograms (ng) of target protein at pH 7.0. Finally, 25 µL of substrate solution was added and the plate (Immulon 2, Dynex) was read in 15 second intervals at 405 nanometers (nm) on a Spectramax 250 plate reader. $IC_{50}$ profiles and values were generated using the program Softmax.

Figure 6:
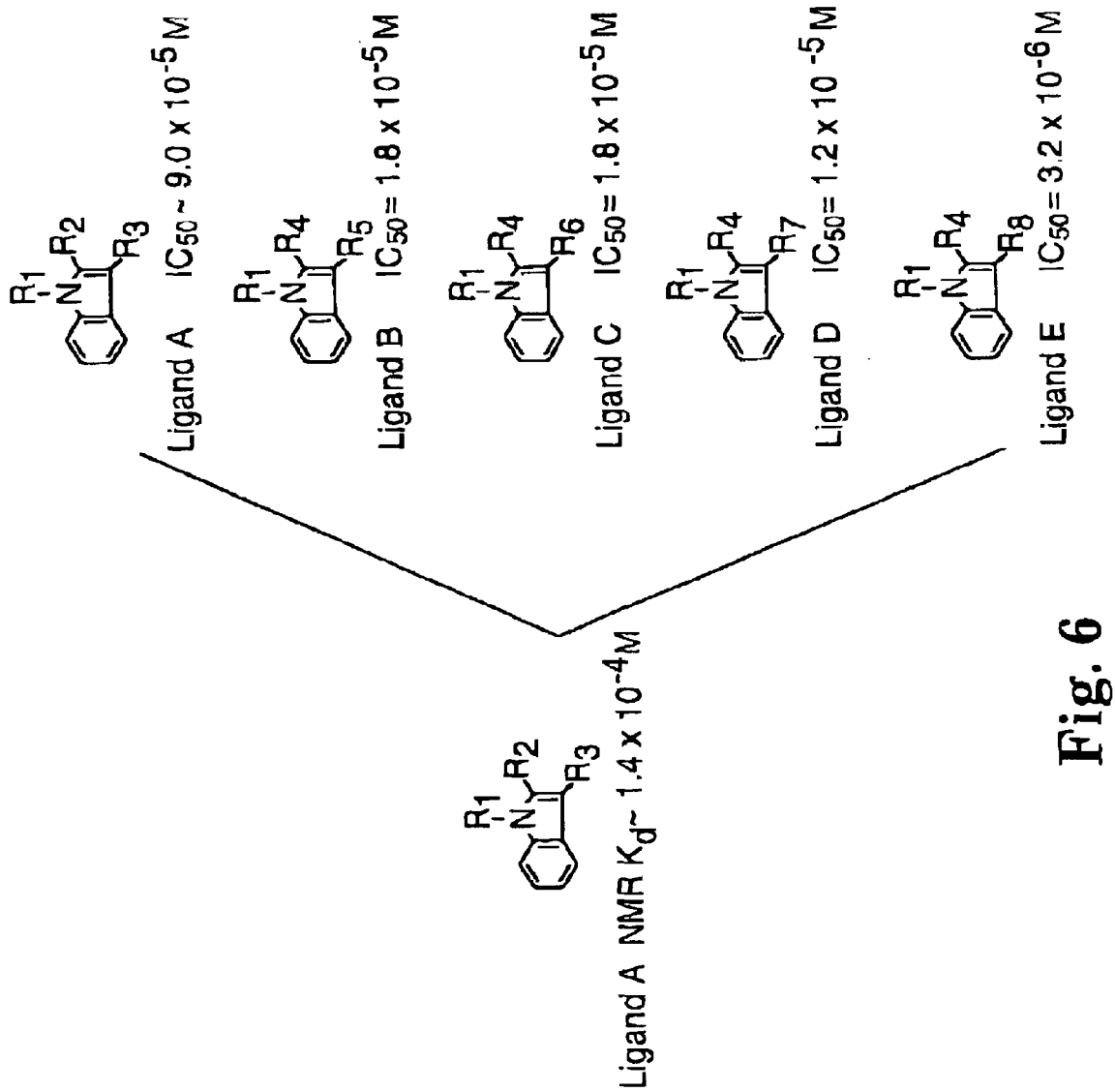
FIG. 6. $IC_{50}$ values of the original ligand, Ligand A, and four structurally related compounds, Ligands B–E, identified in a similarity search based on the structure of Ligand A.

Ligand A was shown to inhibit this enzyme with an $IC_{50}$ value of approximately $9.0 \times 10^{-5}$ M. Subsequently, a similarity search resulted in the testing of about 10 structurally related compounds for enzyme inhibition. As shown in FIG. 6, four of these compounds had $IC_{50}$ values between $2.0 \times 10^{-5}$ M and $1.0 \times 10^{-6}$ M. These very low affinity compounds can serve as lead chemical templates for the design of drugs directed against this molecular target.

Figure 7:
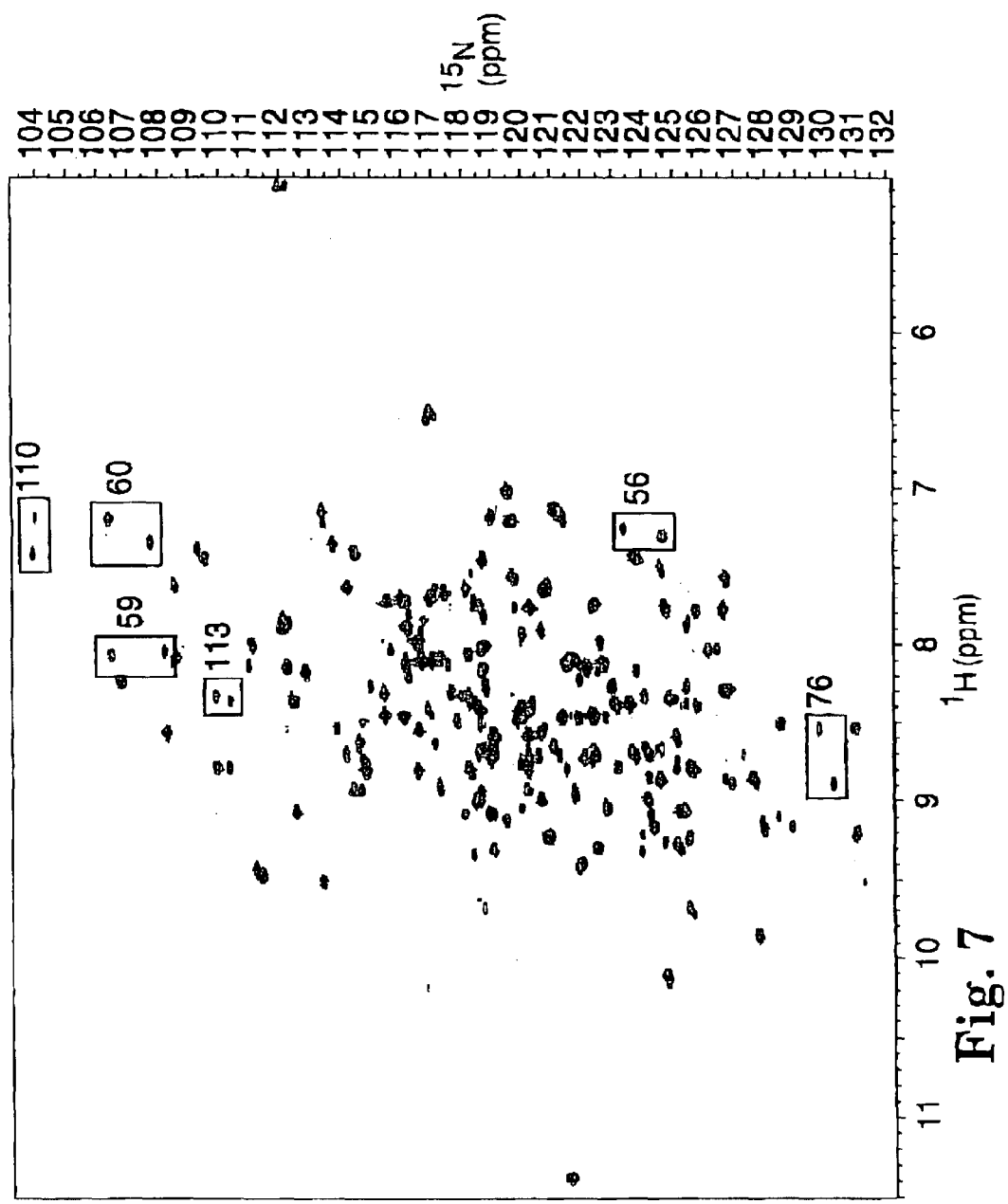
FIG. 7. Region of the 2D $^1H$-$^{15}N$ HSQC spectrum of the antibacterial target protein alone and in the presence of a 10-fold excess of Ligand A. Several resonances with large chemical shift changes in the presence of Ligand A are boxed and labeled with their amino acid sequence number.

Two-dimensional $^1$H-$^{15}$N HSQC spectra were subsequently recorded on [$^{15}$N]target protein with and without Ligand A present to further investigate the interaction of this ligand with the protein. Chemical shift changes observed in the presence of Ligand A are delineated in FIG. 7, which shows an overlay of the $^1$H-$^{15}$N HSQC spectra of protein alone and in the presence of a 10-fold excess of ligand. Residues with the largest ligand-induced chemical shift changes are boxed.

In this study, a ligand that binds to an antibacterial target protein with a dissociation constant of less than about $2.0 \times 10^{-4}$ M was identified from a small library of compounds. No prior knowledge of what types of ligands ought to bind to this protein was used. The identified ligand was shown to inhibit this enzyme with an $IC_{50}$ value of approximately $9.0 \times 10^{-5}$ M. Subsequently, a similarity search based on the structure of this NMR-identified ligand resulted in the testing of about 10 structurally related compounds for enzyme inhibition. Four of these compounds had $IC_{50}$ values between about $2.0 \times 10^{-5}$ M and about $1.0 \times 10^{-6}$ M. These very low affinity compounds can serve as lead chemical templates for the design of drugs directed against this molecular target. More extensive NMR experiments, using isotopically-enriched target protein, concluded that the compounds identified as lead chemical templates do in fact bind to the active site of the target protein.

Example 3

Use of NMR Spectroscopy to Identify a Lead Chemical Template for an Antiviral Target Protein Numerous protein targets are amenable to this NMR process of identifying a lead chemical template. In this example, the technique is illustrated for an antiviral target protein with a monomer molecular weight of approximately 8 kDa that exists as a dimer in solution. This target protein was screened using an NMR screening library and flow NMR spectroscopy.

All solutions containing the antiviral target protein were buffered with $2.0 \times 10^{-2}$ M phosphate at pH 6.5. The protein used for the 1D screening and dissociation constant determination experiments was unlabeled, while that used for the 2D $^1$H-$^{15}$N HSQC experiments was $^{15}$N-enriched.

One-dimensional relaxation-edited $^1$H NMR spectra of samples containing a mixture of the target protein and a given compound combination were recorded in $^2$H$_2$O solution on a Bruker AMX-400 spectrometer. The spectrometer was equipped with a shielded magnet, a Gilson sample handler, and a 5 mm (250 µL sample cell) flow-injection NMR probe. A spin lock time of 350 milliseconds was used. The screening experiments were carried out on solutions that were $3.8 \times 10^{-5}$ M target protein and $5.0 \times 10^{-5}$ M of each ligand. All solutions were contained in a 96-well plate and were delivered to the 5 mm flow-injection probe using the Gilson sample handler. The library used for the screening process was expanded from that described in the first two examples. It contained approximately 300 compounds grouped into 32 separate mixtures.

Two-dimensional $^1$H-$^{15}$N HSQC spectra were recorded in $^1$H$_2$O solution on a Bruker DRX-500 spectrometer. Samples contained $8.3 \times 10^{-4}$ M target protein alone or in the presence of a given ligand.

Ligand dissociation constants were estimated by determining relative diffusion coefficients for target protein alone, ligand in the absence of target protein, and ligand in the presence of target protein (Lennon et al., *Biophys. J.*, 67, 2096–2109 (1994)). Relative diffusion coefficients were determined using pulsed-field-gradient NMR experiments incorporating a bipolar longitudinal eddy-current delay sequence (Wu, *J. Magn. Reson. Ser. A*, 115, 260–264 (1995)).

One-dimensional relaxation-edited $^1$H NMR spectroscopy was used to screen the expanded small molecule library for binding to this antiviral target protein in a manner analogous to that previously described in the first two examples. With this technique, a reduction in resonance intensity is observed if a compound interacts with the target protein, thus identifying it as a ligand. For most of the compound combinations in the presence of the antiviral target protein, there was little or no reduction in resonance intensity with the 350-millisecond spin-lock time. However, for some of the compound combinations, the intensities of resonances corresponding to one of the compounds in the mixture were significantly reduced. The results from one such compound combination are described here.

As a control, the 1D relaxation-edited $^1$H NMR spectrum of a certain mixture in the absence of protein is shown in FIG. 8A. All resonances are observed with full intensity. The corresponding 1D relaxation-edited $^1$H NMR spectrum acquired in the presence of the antiviral target protein is shown in FIG. 8B. The intensities of all resonances corresponding to a single compound in FIG. 8B are clearly reduced in the presence of the antiviral target protein. This indicates that this compound is binding to the protein. The binding is specific to the antiviral target protein since the resonance intensities are not reduced in the presence of other protein targets that have been screened.

In a separate set of experiments that use pulsed-field-gradient techniques to determine relative diffusion coefficients, the dissociation constant for the identified ligand was estimated by NMR measurements to be approximately 40 µM.

Figure 9:
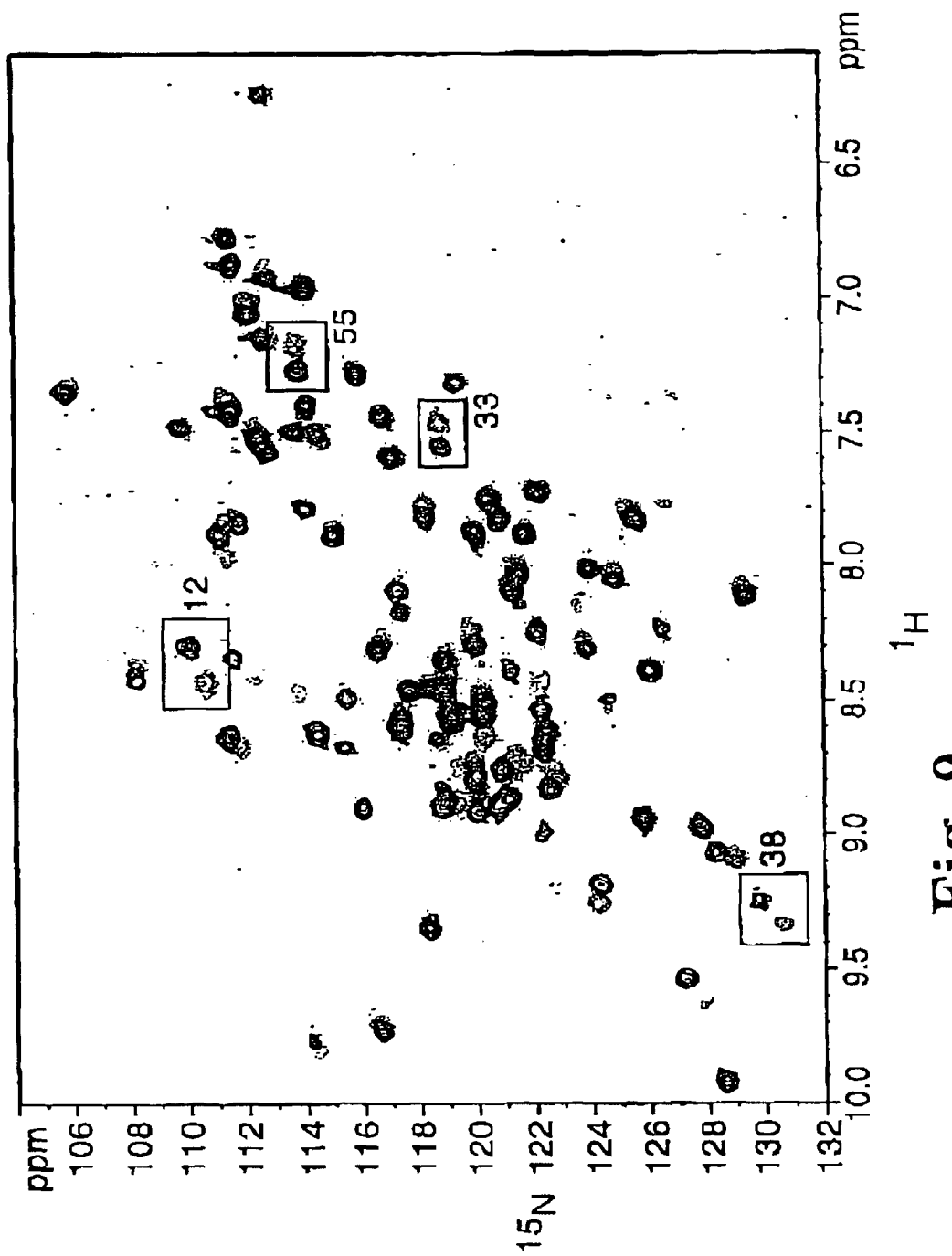
FIG. 9. Region of the 2D $^1H$-$^{15}N$ HSQC spectrum of the antiviral target protein alone and in the presence of the ligand identified from FIG. 8. Several resonances with large chemical shift changes in the presence of this ligand are boxed and labeled with their amino acid sequence number.

Two-dimensional $^1$H-$^{15}$N HSQC spectra were subsequently recorded on [$^{15}$N]target protein with and without the identified ligand present to further investigate the interaction of this ligand with the protein. Chemical shift changes observed in the presence of this ligand are delineated in FIG. 9, which shows an overlay of the $^1$H-$^{15}$N HSQC spectra of protein alone and in the presence of ligand. Residues with the largest ligand-induced chemical shift changes are labeled.

Example 4

Screening of Compound Libraries for Protein Binding Using Flow-Injection NMR Spectroscopy Introduction Flow NMR spectroscopy techniques are becoming increasingly utilized in drug discovery and development (B. J. Stockman, Curr. Opin. Drug Disc. Dev., 3, 269–274 (2000)). The technique was first applied to couple the separation characteristics of liquid chromatography with the analytical capabilities of NMR spectroscopy (N. Watanabe et al., Proc. Jpn. Acad. Ser B, 54, 194 (1978)). Since then, HPLC-NMR, or LC-NMR as it is more commonly referred to, has been broadly applied to natural products biochemistry, drug metabolism and drug toxicology studies (J. C. Lindon et al., Prog. NMR Spectr., 29, 1 (1996); J. C. Lindon et al., Drug. Met. Rev., 29, 705 (1997); B. Vogler et al., J. Nat. Prod., 61, 175 (1998); and J.-L. Wolfender et al., Curr. Org. Chem. 2, 575 (1998)). The wealth and complexity of data made available from the latter two applications have created the potential for NMR-based metabonomics to complement genomics and proteomics (J. K. Nicholson et al., Xenobiotica, 29, 1181 (1999)). Stopped-flow analysis in LC-NMR, where the chromatographic flow is halted to obtain an NMR spectrum with higher signal-to-noise and then restarted when the spectrum has finished collecting, was the forerunner to the flow-injection systems that will be described here. The largest difference between the two systems is that one includes a separation component (LC column) and the other does not. The rapid throughput possible for combinatorial chemistry samples and protein/small molecule mixtures has allowed flow-injection NMR methods to impact medicinal chemistry and protein screening (P. A. Keifer, Drugs Fut., 23, 301 (1998); P. A. Keifer, Drug Disc. Today, 2, 468 (1997); P. A. Keifer, Curr. Opin. Biotech., 10, 34 (1999); K. A. Farley et al., SMASH'99, Argonne, IL, 15–18 August 1999; and A. Ross et al., Biomol. NMR, 16, 139 (2000)).

Changes in chemical shifts, relaxation properties or diffusion coefficients that occur upon the interaction between a protein and a small molecule have been documented for many years (for recent reviews see M.J. Shapiro et al. Curr. Opin. Drug. Disc. Dev., 2,396(1999); J. M. Moore, Biopolymers, 51, 221(1999); and B. J. Stockman, Prog. NMR Spectr., 33, 109(1998). Observables typically used to detect or monitor the interactions are chemical shift changes for the ligand or isotopically-enriched protein resonances (J. Magn. Reson., 34, 669(1979); and T. Scherf et al., J. Am. Chem. Soc., 94, 4017(1972); and A.A. Bothner-By et al., Ann. Ny Acad. Sci. 222, 668(1973)), or restricted diffusion (A. J. Lennon et al., Biophys., J. 67, 2096 (1994)) for the ligand. For the most part, these studies have focused on protein/ligand systems where the small molecule was already known to be a ligand or was assumed to be one. In the last several years, however, the work of the Fesik (s. B. Shuker et al., Science, 274, 1531 (1996); and P. J. Hajduk et al., J. Am. Chem Soc., 119, 12257 (1997), Meyer et al., Eur. J. Biochem., 246, 705 (1997). Moore (J. Fejzo et al., Chem. Biol., 6, 755(1999)), Shapiro (M. Lin et al., J. Org. Chem., 62, 8930(1997)), and Dalvit (C. Dalvit et al., J. Biomol NMR, 18, 65–68 (2000)) labs has demonstrated the applicability of these same general methods as a screening tool to identify ligands from mixtures of small molecules.

These screening protocols typically involve the preparation of a series of individual samples in glass NMR tubes and the use of an autosampler to achieve reasonable throughput. Variations in volume or positioning that occur during sample preparation or tube insertion can necessitate tuning and calibration of the probe between each sample, thereby reducing throughput of data collection.

By contrast, flow-injection NMR has several advantages. The stationary flow cell provides uniform locking and shimming from one sample to the next, and, with the radio frequency coils mounted directly onto the flow cell's glass surface, high sensitivity. Fast throughput of data collection is thus possible. Use of a liquid handler to prepare and inject samples, such as the Gilson 215 liquid handler used on Bruker and Varian systems, allows the potential for on-the-fly sample preparation (A. Ross et al., J. Biomol. NMR, 16, 139 (2000)), thus maximizing sample integrity and uniformity. Since the use and/or re-use of glass NMR tubes is avoided, costs are minimized.

Data Acquisition Hardware and Software

Figure 10:
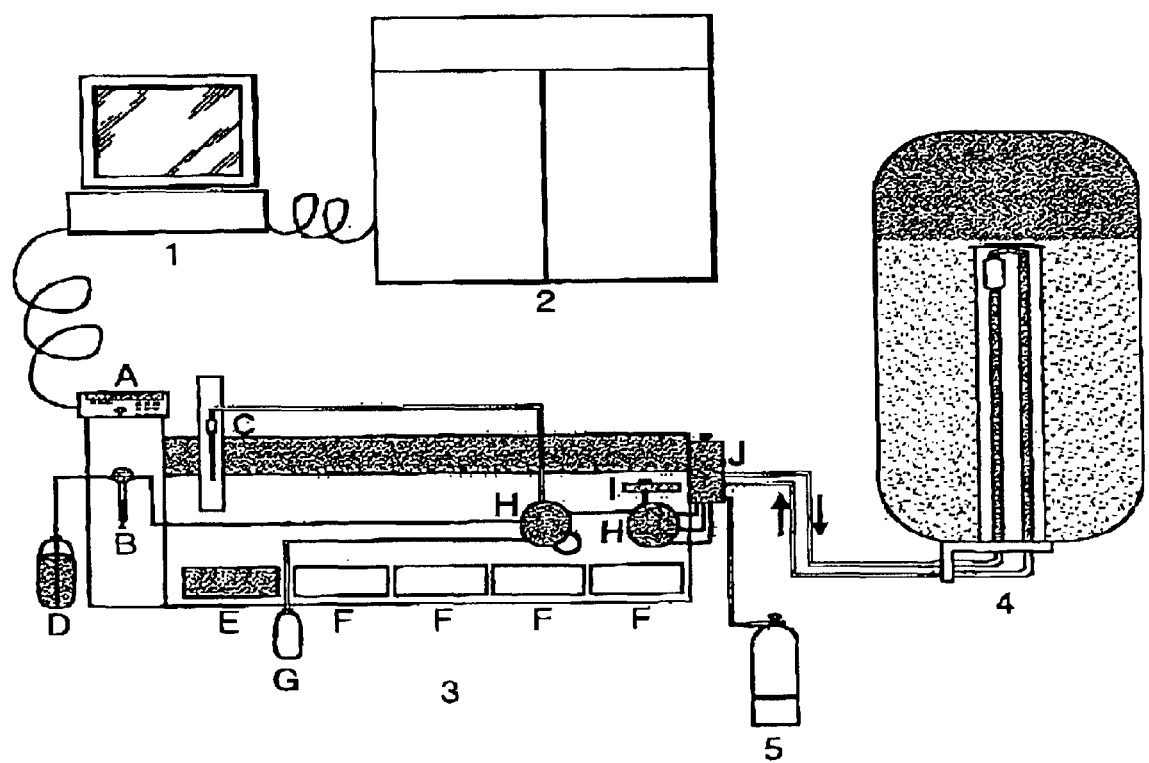
FIG. 10. Schematic of the BEST flow system: (1) computer workstation, (2) NMR console, (3) Gilson sample handler, (4) flow probe in the magnet, and (5) nitrogen gas. The Gilson sample handler is labeled as follows: (A) keypad, (B) syringe, (C) injector, (D) solvent reservoir, (E) solvent rack, (F) sample racks, (G) waste reservoir, (H) Rheodyne valves, (I) injection port, and (J) recovery unit.

A typical Flow NMR system consists of a magnet, an NMR console, a computer workstation, a Gilson sample handler, and a flow-injection probe. Two vendors currently offer complete flow-injection systems: Bruker Instruments and Varian Instruments. In addition, the Nalorac Corporation manufactures an LC probe that can also be used for flow-injection NMR screening. A schematic of the Bruker Efficient Transport System (BEST) manufactured by Bruker Instruments is shown in FIG. 10. The Gilson 215 sample handler supplied by Bruker is equipped with two Rheodyne 819 valves. The first valve is attached to a 5 ml syringe, the needle capillary in the sample handler injection arm, the bridge capillary, the waste reservoir, and the second valve. The second Rheodyne valve is attached to the input and output of the probe, the source of nitrogen gas, the first valve, and the injection port. FEP Teflon tubing is used in each of the connections with the exception of the gas connection, which uses PEEK tubing.

A sample is injected into the Bruker probe by filling the needle capillary and transferring the sample into the inlet tubing for the probe using the second Rheodyne valve. In quick mode, the next sample is loaded into the tubing during the spectral acquisition of the previous sample. When the spectral acquisition has completed, the first sample exits the probe through the outlet capillary. This action pulls the next sample into the probe through the inlet port and spectral acquisition can immediately begin. Quick mode acquisition can save approximately one minute per sample from the time it would take to load each sample individually. However, sample recovery is not currently an option with this method. In order to recover a sample, each sample is injected individually using normal mode acquisition. The sample is recovered by selecting either nitrogen gas or the syringe to pull the sample back from the probe through the inlet tube. The sample can then be returned to the Gilson liquid handler into its original well or into a new 96 well plate. A recovery unit has recently been added to the BEST system to improve the efficiency of recovery of the syringe by using the nitrogen gas to create a back pressure on the sample.

Two useful accessories available for the BEST system are a Valvemate solvent switcher and a heated transfer line. The solvent switcher was added to the flow system for the combinatorial chemist who may want to analyze samples in various organic solvents, but it can also be used for a library screen to vary buffer conditions or to clean the probe out with an acid or a base. The heated transfer line is used to equilibrate the sample temperature to the probe temperature during sample transfer. Both the inlet and output capillary transfer lines are threaded through the heated transfer line. This feature is desirable when the spectral analysis time is short and a high throughput of samples is required. In the ideal case, data acquisition using this accessory can begin immediately after the sample enters the probe. Some samples may still require a temperature equilibration period after entering the probe.

The setup of the Versatile Automated Sample Transport (VAST) system produced by Varian is similar to the Bruker system. The VAST system consists of a Gilson 215 liquid handler, a Varian NMR flow probe, an NMR console, and a Sun workstation. The Gilson liquid handler supplied by Varian is equipped with a single Rheodyne 819 valve and is connected to the NMR flow probe with 0.010 inch inside diameter PEEK tubing (P. A. Keifer et al., *J. Comb. Chem.*, 2, 151 (2000)). In the Varian system design, the sample handler injects a specified volume of sample into the probe, the data is acquired, and then the flow of liquid through the tubing is reversed and the sample is returned to its original vial or well. The return of the sample to the Gilson by the syringe pump is assisted by a Valco valve and nitrogen gas which supply some backpressure on the outlet portion of the Varian flow probe. With the VAST system setup, the probe is rinsed just prior to sample injection and then is dried with nitrogen gas to minimize dilution of the sample during injection. The Varian design gives excellent sample recovery without dilution, but it is strongly recommended that samples be filtered to prevent clogging of the capillary transfer lines (P. A. Keifer et al., *J. Comb. Chem.*, 2, 151 (2000)).

Flow NMR systems are ideally suited for use with the shielded magnets manufactured by Bruker Instruments or Oxford Magnets. Actively shielding a 600 MHz magnet reduces the radial 5 gauss line from approximately 4 meters to less than 2 meters, which allows the Gilson liquid handler to be placed significantly closer to the magnet. This reduces the length of tubing needed between the Rheodyne valve and the flow-injection probe and minimizes the sample transfer time. The potential for clogging and sample dilution are concomitantly reduced.

Bruker uses two software packages to run the BEST system: BEST Administrator and ICONNMR (Bruker Instruments, AMIX, BEST and ICONNMR software packages). The BEST administrator is activated by typing the command 'BESTADM' in XWINNMR. This portion of the software is used during method generation and optimization. Samples are injected into the probe one at a time and data is collected under XWINNMR. Early versions of the BEST software utilized three separate programs: CFBEST, SUBEST, and OTBEST. These functions were recently combined under the single software package, BEST Administrator. In addition, the parameters available for customization have been greatly expanded to include automated solvent switching and method switching, which were not available in earlier versions of the software. The software package ICONNMR is used after a flow method has been optimized with the BEST administrator. This package is setup for full automation and is the same software used with automated NMR tube sample changers. In a similar fashion, Varian software uses the command 'Gilson' to generate a method before sample injection and data acquisition is initiated using Enter/Autogo in VNMR (Varian NMR Systems, VNMR software package).

Flow Probe Calibration and System Optimization

Figure 11:
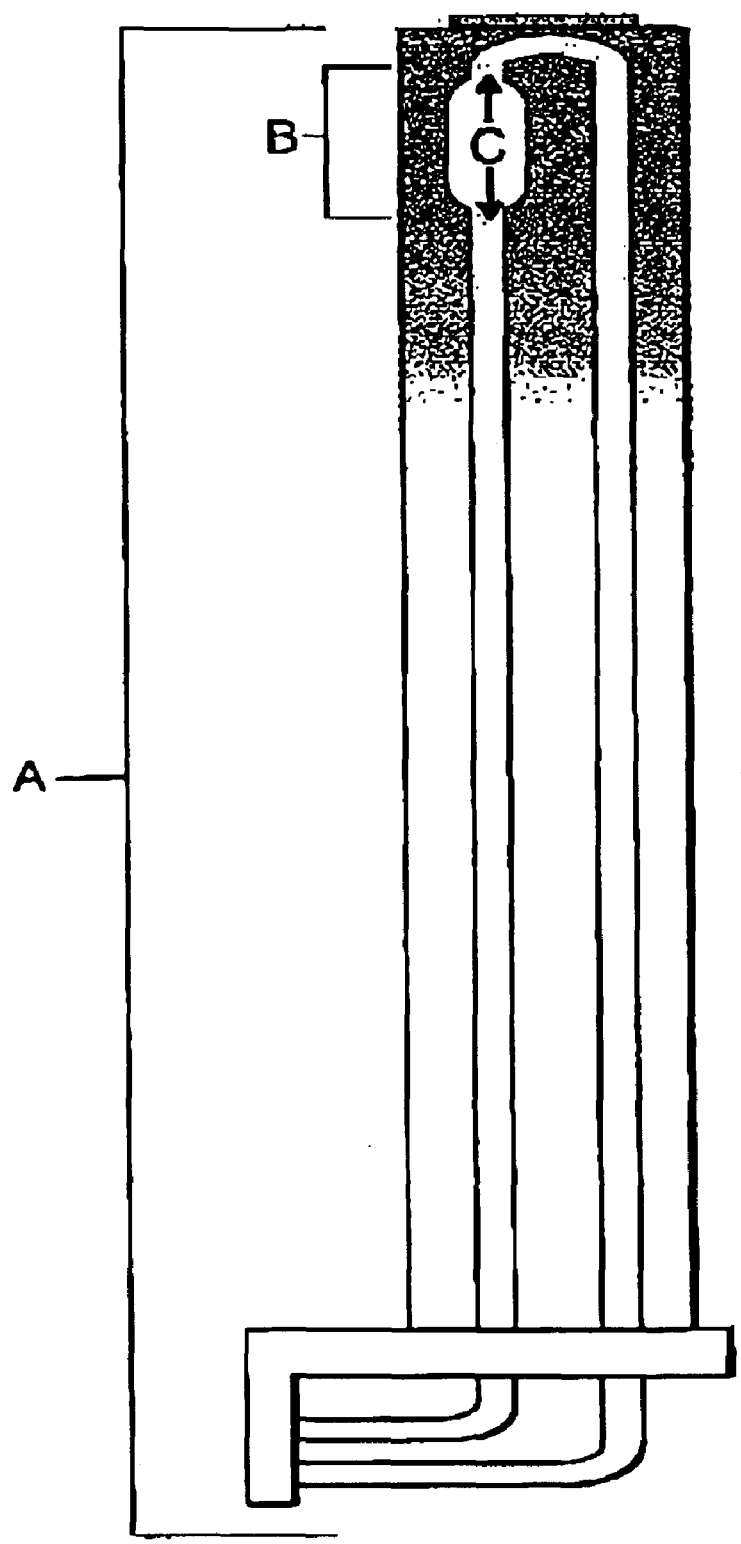
FIG. 11. Schematic of a Bruker flow probe showing (A) the total probe volume, (B) the flow cell volume, and (C) the positioning volume.

In addition to the normal 90° pulse lengths and power levels which are calibrated for any NMR probe, several additional calibrations are required for a flow probe. The three additional volumes required to calibrate a Bruker flow probe are shown schematically in FIG. 11 (Bruker Instruments, AMIX, BEST and ICONNMR software packages). The first volume calibrated is the total probe volume. This can be accomplished by injecting a colored liquid into the inlet of a dry probe with a syringe and watching for the liquid to appear in the outlet port (approximately 700–800 $\mu$L for a 5 mm flow probe). With the Varian system, the system filling volume also includes the capillary tubing that connects the injector port to the flow probe (P. A. Keifer et al., *J. Comb. Chem.*, 2, 151 (2000)). This volume is used to calculate the distance required to reposition a sample from the Gilson sample handler to the center of the flow cell in the probe.

The second volume calibrated is the flow cell volume. This is the volume of liquid required to fully fill the coil around the flow cell. The three flow probe vendors (Bruker, Varian, and Nalorac) have probes available with active volumes ranging from 30–250 $\mu$L. The stated volume of the flow cell in a 5 mm Bruker flow probe is 250 $\mu$L, but it was calibrated to be approximately 300 $\mu$L. This volume can be calibrated by making repeated injections of a standard sample, starting with a volume less than the stated active volume of the probe, and collecting a 1D $^1$H NMR spectrum. The injection volume can then be increased incrementally until no further improvement in signal-to-noise is observed.

Figure 12A:
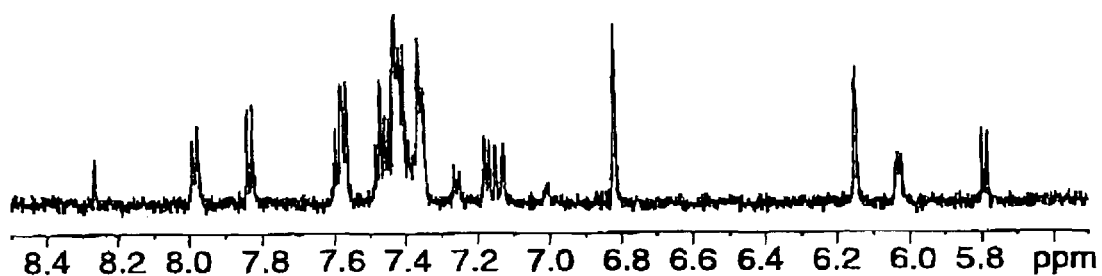
FIG. 12. 600.13 MHz $^1H$ NMR spectra of a 100 $\mu$M NMR library sample with the positioning volume set to (A) –100 $\mu$l, (B) 0 $\mu$l, and (C) +100 $\mu$l.
Figure 12B:
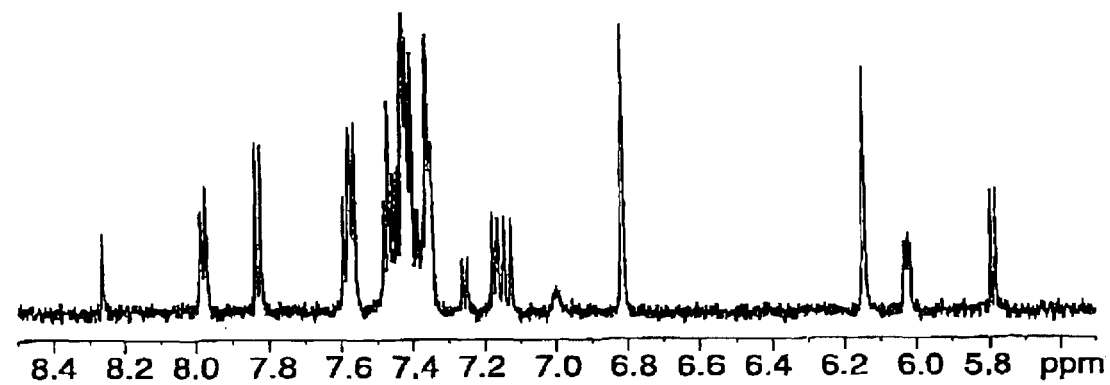
Figure 12C:
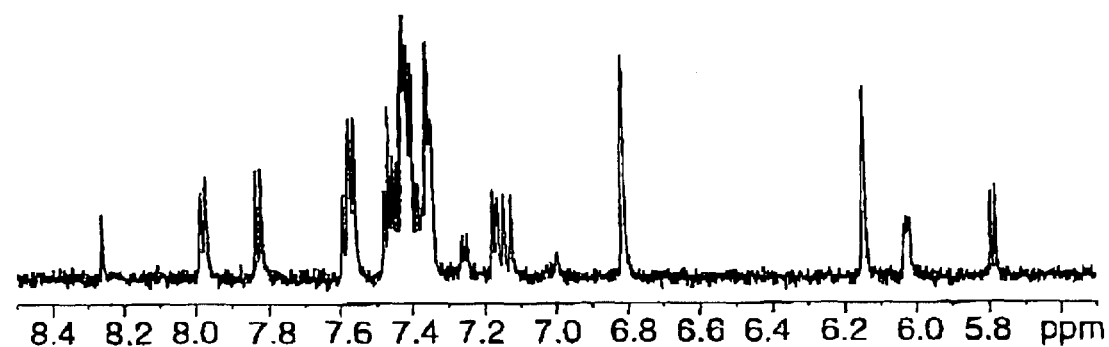

In addition to the two probe volume calibrations already discussed, Bruker software also includes a third volume for calibration. This volume, referred to as the positioning volume, is used to optimize the centering of a sample in the flow cell. Early versions of ICONNMR software (prior to 3.0.a.9) did not include the ability to set the positioning volume. Rather, Bruker literature suggested that the flow cell volume should be roughly doubled to insure that the sample would completely fill the coil (Bruker Instruments, AMIX, BEST and ICONNMR software packages). Fortunately, this is no longer necessary. The positioning volume can now be used to optimize the sample position. This calibration reduced the sample size required for injection from 450 $\mu$L in the first few protein screens to 300 $\mu$L for current screens using a Bruker 5 mm flow probe with an active volume of 250 $\mu$L. Optimization of this parameter minimized the sample volume required for each spectrum. Importantly, this significantly reduced the total amount of protein (or other target) at a given concentration needed to screen our small molecule library. The positioning volume can be optimized by collecting a series of spectra on a standard sample. In each spectrum collected, the positioning volume can first be varied by large increments (50–100 $\mu$L) to get a rough estimate of the volume. An example of three such spectra is shown in FIG. 12. The positioning volume can then be varied in smaller increments (10–25 $\mu$L) to identify the best volume for this parameter. The best signal-to-noise was obtained for our 5 mm Bruker flow probe on a DRX-600 when the positioning volume was set to +25 $\mu$L, but this volume is probe specific and is calibrated for each flow probe.

The optimization of a flow-injection system for screening has three main objectives. The first objective is to transfer an aqueous sample to the center of the flow cell for analysis using the parameters determined during the flow probe calibration described above. The second objective is to reposition a sample from the Gilson liquid handler into the flow-injection probe without bubbles and with minimal sample dilution. This can be achieved by using nitrogen as a transfer gas (which keeps the system under pressure) and by using a series of leading and trailing solvents. In our experiments, we typically use 150 $\mu$L of $^2$H$_2$O as a leading solvent, 20 $\mu$L of nitrogen gas, 300 $\mu$L of sample, 20 $\mu$L of nitrogen gas, and 100 $\mu$L of $^2$H$_2$O as a trailing solvent. Alternatively, a larger volume of sample can be used in place of the push solvents. The third objective is to determine a cleaning procedure which would reduce sample carry-over to less than 0.1%. Typically, this involves rinsing the probe with a predetermined volume of water. The rinse cycle can also be followed by a dry cycle, in which the capillary lines and flow probe are dried with nitrogen gas to further minimize sample dilution. In our experiments, we typically use a 1-mL wash volume followed by a 30 second drying time with nitrogen gas.

Design of Small Molecule Screening Libraries

With the increasing prevalence of extremely high throughput screening equipment in the pharmaceutical industry, it may seem counter intuitive to suggest screening smaller collections of compounds in an NMR-based assay. However, a correlation between the quality of hits obtained and the number of compounds screened has not been well documented. In fact, compounds are typically added to screening collections not to simply increase their numbers, but to increase the diversity and quality of the compound collection. Thus, if one could find suitable hits from a smaller collection of well-chosen compounds, it may not be necessary to expend the time and chemical resources to screen the entire compound library against every single target. Hits so identified could then be used to focus further screening efforts or to direct combinatorial syntheses, thus saving both time and chemical resources, as shown schematically in FIG. 1. An NMR-based screen, like other binding assays, has the advantage in that a high throughput functional assay does not need to be developed. This will become increasingly important as more and more targets of interest to pharmaceutical research are derived from genomics efforts and thus may not have a known function that can be assayed.

Several types of libraries are possible: broad screening libraries applicable to many types of target proteins, directed libraries that are designed with the common features of an active site in mind that might be useful for screening a series of targets from the same protein class, such as protease enzymes, and "functional genomics" libraries composed of known substrates, cofactors and inhibitors for a diverse array of enzymes that might be useful for defining the function of genomics-identified targets.

Ideally, the size and content of a broad screening library should be such that screening can be accomplished in a day or two with a favorable chance of identifying several hits for each of the target proteins to be screened. Rather than just randomly choosing a subset library, several rationale approaches have been implemented. These include the SHAPES library developed by Fejzo and coworkers that is composed largely of molecules that represent frameworks commonly found in known drug molecules (J. Fejzo et al., *Chem. Biol.*, 6, 755 (1999)), drug-like or lead-like libraries, and diversity-based libraries. A number of studies have recently appeared that discuss the properties of known drugs and methods to distinguish between drug-like and non-druglike compounds (G. W. Bemis et al., *J. Med. Chem.*, 39, 2887 (1996); C. A. Lipinski et al., *Adv. Drug Del. Rev.*, 23, 3 (1997); Ajay et al., *J. Med. Chem.*, 41, 3314 (1998); J. Sadowski et al., *J. Med. Chem.*, 41, 3325 (1998); A. K. Ghose et al., *J. Comb. Chem.*, 1, 55 (1999); J. Wang et al., *J. Comb. Chem.*, 1, 524 (1999); and G. W. Bemis et al., *J. Med. Chem.*, 42, 5095 (1999)). Superimposing drug-like (E. J. Martin et al., *J. Comb. Chem.*, 1, 32 (1999)) or lead-like (S. J. Teague et al., *Angew. Chem. Int. Ed.*, 38, 3743 (1999)) properties on a diversity-selected compound set may yield the best library of compounds. The distinction of lead-like is important since the NMR-based assay is designed to identify weak-affinity compounds that will most likely gain molecular weight and lipophilicity to become drug candidates or even lead chemical templates (S. J. Teague et al., *Angew. Chem. Int. Ed.*, 38, 3743 (1999)).

Development and expansion of our lead-like NMR screening library to mimic the structural diversity of our larger compound collection has made use of the DiverseSolutions software for chemical diversity (R. S. Pearlman et al., *Persp. Drug Disc. Des.*, 9/10/11, 339 (1998)). In this approach, each compound is described by a set of descriptors, which are metrics of chemistry space. Six orthogonal descriptors, related to substructures as opposed to the entire molecule, are often used. While the descriptors to use can be automatically chosen to maximize diversity, typically there are two each corresponding to charge, polarizability and hydrogen-bonding. A cell-based diversity algorithm is employed to divide the descriptor axes into bins and thus into a lattice of multidimensional hypercubes. As an example of how this can be used to construct or expand a small screening library, consider the selection of 1,000 compounds from a compound library of 250,000 compounds. First, the cell-based algorithm is used to partition the 250,000 compounds into approximately 1,000 cells. The number of compounds per cell will vary and some will be empty. Maximum structural diversity will be obtained by taking one compound from each occupied cell (and as close to the center as possible). The actual compounds chosen are based on desirable lead-like properties such as low molecular weight and hydrophilicity as well as availability and chemical non-reactivity as explained below. Diversity voids, as exemplified by empty cells, can be filled from external sources or by chemical syntheses if desired. Identifying and filling diversity voids is important since larger compound collections are often heavily weighted in certain classes of compounds stemming from earlier research projects.

Figure 13:
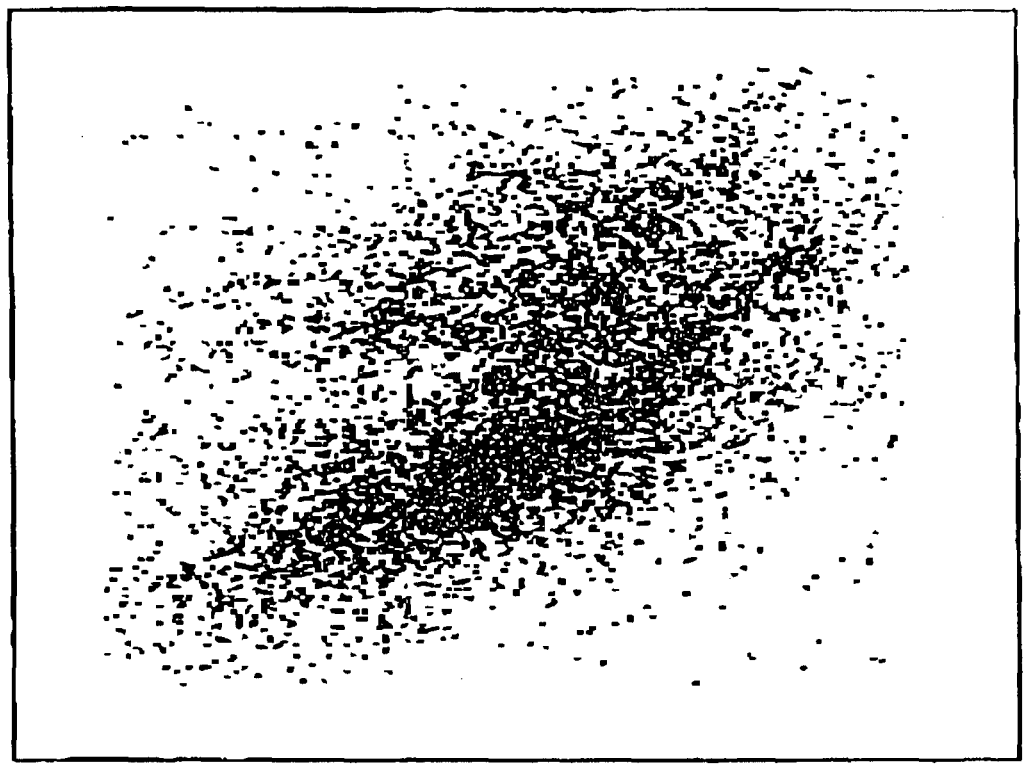
FIG. 13. Overlay of the two-dimensional HA (hydrogen-bond acceptor) vs. CHRG (charge) BCUT plots for the compounds in the CMC index (gray) and the lead-like compounds contained therein (black).

An example of diversity-based subset selection using these methods is shown in FIG. 13. Here, the 6,436 compounds from the Comprehensive Medicinal Chemistry index have been divided into 2,012 cells to maximize diversity using five chemistry-space descriptors. The two-dimensional representation projected onto the hydrogen bond acceptor and charge BCUT axes is shown in gray. The black squares correspond to the 1,474 lead-like compounds (molecular weight less than 350 and 1<cLogP<3) contained in the CMC index. A total of 806 of the 2,012 cells were occupied by lead-like compounds. A similar approach could be used to select diverse, lead-like compounds from a large corporate compound collection.

The cell concept of structural space is quite useful after the screening is complete. When a hit is identified, other compounds from the same or nearby cells are obvious candidates for secondary assays. One can think of this as the gold mine analogy: when gold is struck, the search is best continued in close proximity.

In addition to structural diversity, there are other characteristics that can be considered when selecting the subset molecules. These include purity, identity, reactivity, toxicological properties, molecular weight, water solubility, and suitability for chemical elaboration by traditional or combinatorial methods. It makes sense to populate the screening library with compounds of high integrity that are not destined for failure down the road. Time spent upfront to insure purity and identity with LC-MS or LC-NMR analyses will save resources downstream. Filtering tools can be used to avoid compounds that are known to be highly reactive, toxic, or to have poor metabolic properties. Lack of reactivity is important since compounds can be screened more efficiently as mixtures. Like other labs (S. B. Shuker et al, *Science*, 274, 1531 (1996); B. Meyer et al., *Eur. J. Biochem.*, 246, 705 (1997); J. Fejzo et al., *Chem. Biol.*, 6, 755 (1999); and M. Lin et al., *J. Org. Chem.*, 62, 8930 (1997)) we typically pool our selected small molecules into mixtures of 6–10 compounds for screening (K. A. Farley et al., SMASH'99, Argonne, IL, Aug. 15–18, 1999).

Compounds chosen for our diversity library are lead-like as opposed to drug-like. It is often the case that chemical elaborations to improve affinity also increase molecular weight and decrease solubility (S. J. Teague et al., *Angew. Chem. Int. Ed.*, 38, 3743 (1999)). The molecular weight of the compounds therefore should preferably not exceed about 350. Since most hits obtained will have affinities for their target in the approximately 100 $\mu$M range, low molecular weight will leave room for chemical elaboration to build in more affinity and selectivity. Using larger molecular weight drug-like compounds would not substantially improve affinity of the hits and could easily preclude obtaining lead chemical templates of reasonable size. Lead-like hits that are reasonably water soluble allow for chemical elaboration that results in modest increased lipophilicity of the final therapeutic entity (S. J. Teague et al., *Angew. Chem. Int. Ed.*, 38, 3743 (1999)). Water solubility is also important since it enhances the potential success of downstream studies such as calorimetry, enzymology, co-crystallization and NMR structural studies. Compound solubility is especially important for flow-injection NMR methods in order to prevent clogging of the capillary lines.

Compounds should also be chosen with their suitability for chemical elaboration by traditional or combinatorial chemistry methods in mind. Hits with facile handles for synthetic chemistry will be of more interest and will allow more efficient use of often limited medicinal chemistry resources.

Relaxation-Edited or WaterLOGSY-Based Flow-Injection NMR Screening Methods

Calibration and validation of the flow system and creation of a small-molecule screening library yields an automated system that is ready to screen new targets. A protein target can be analyzed for protein-ligand interactions using relaxation-editing methods by adding sufficient protein to each well of the 96-well library plate to give a 1:1 (protein:ligand) ratio at a concentration of approximately 50 $\mu$M. Homogeneous sample dispersion throughout the well can be facilitated by agitating the plate on a flat bed shaker. Screening at this concentration allows a decent 1D $^1$H NMR spectrum to be acquired in about 10 minutes. In our experience, this concentration of target and small molecule requires identified ligands to have affinities on the order of approximately 200 $\mu$M or tighter.

Figure 14A:
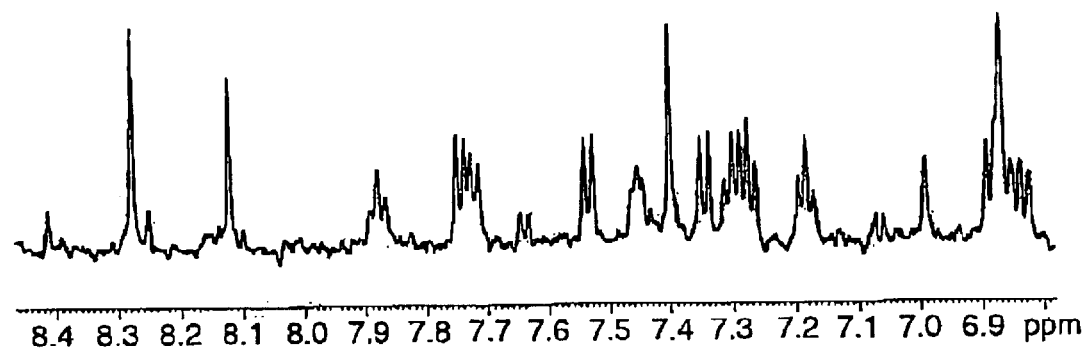
FIG. 14. Regions of the 600.13 MHz relaxation-edited $^1H$ NMR spectra of a nine compound mixture (A) without and (B) with added target protein. Protein and each ligand were 50 $\mu$M. Spectra were acquired on a Bruker 5 mm flow-injection probe at 27° C. A total of 1K scans were collected resulting in a total acquisition time of about 60 minutes per spectrum. A relaxation filter of 174 milliseconds (ms) was used. Arrows identify resonances that disappear in the presence of protein.
Figure 14B:
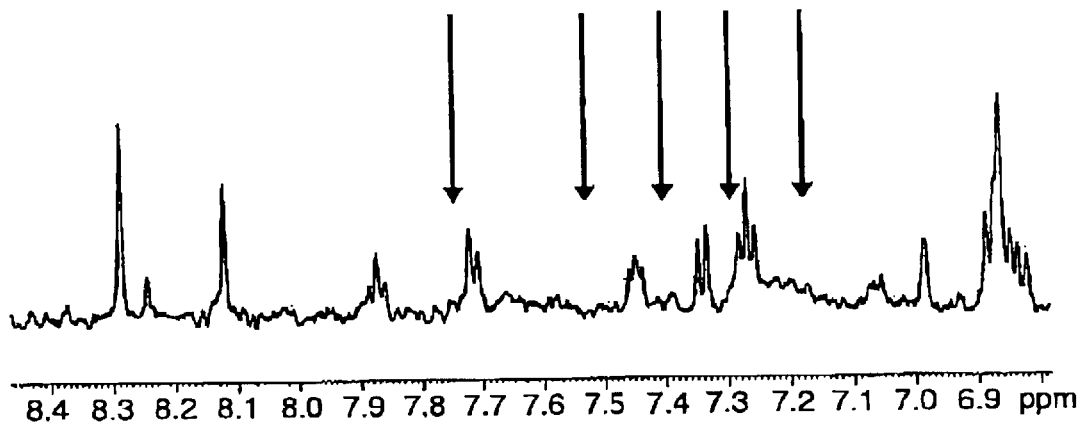

Once the screening plate has been prepared, the Gilson liquid sample handler transfers samples from 96-well plates into the flow-injection probe and if desired, returns the samples back into either the original 96-well plate or a new plate. Once the sample is in the magnet, spectra that can detect changes in chemical shifts, relaxation properties, or diffusion properties can be collected. In our relaxation-edited NMR screening assay, two 1D relaxation-edited $^1$H NMR spectra are collected: one spectrum is collected on the ligand mixture in the presence of protein and the second, control spectrum is collected on the ligand mixture in the absence of protein. Ligands are identified as binding to a target when their resonances are greatly reduced when compared to a relaxation-edited spectrum collected in the absence of protein as illustrated in FIG. 14. In this example, the target protein was a genomics-derived protein of unknown function.

Figure 15A:
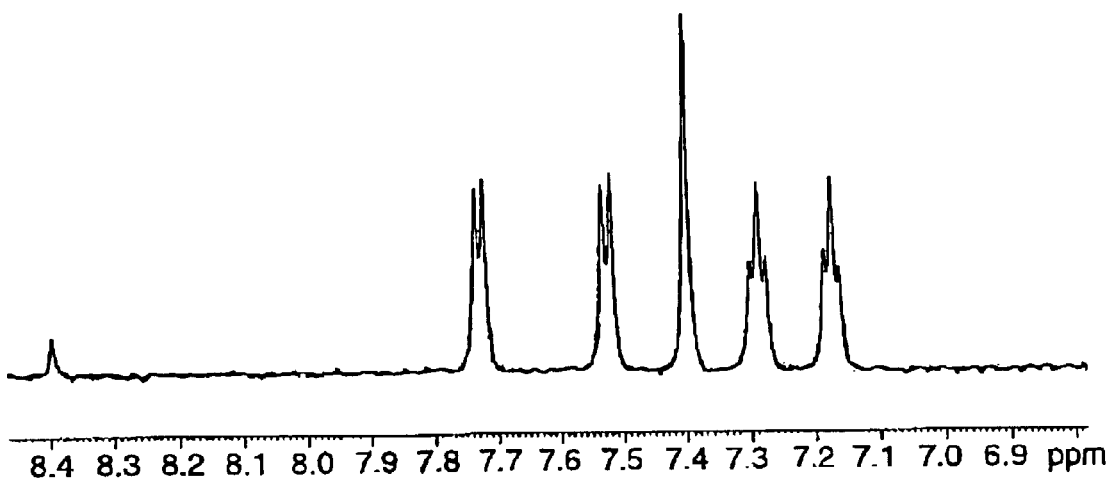
FIG. 15. Regions of the 600.13 MHz relaxation-edited $^1H$ NMR spectra of a single compound (A) without and (B) with added target protein. Protein and ligand were 50 $\mu$M. Spectra were acquired on a regular Bruker 5 mm TXI probe at 27° C. A total of 512 scans were collected resulting in a total acquisition time of about 30 minutes per spectrum. A relaxation filter of 174 ms was used.
Figure 15B:
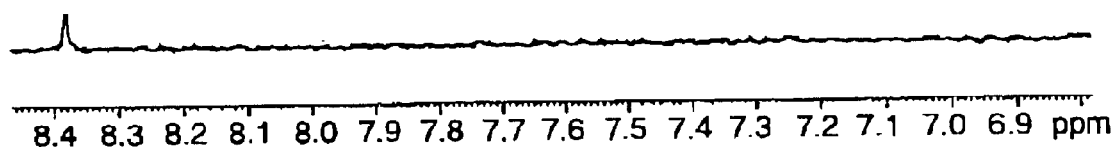

Ligand binding can be confirmed by collecting a 1D relaxation-edited $^1$H NMR spectrum of each individual ligand that was identified as binding to the protein in a given mixture as shown in FIG. 15. In addition, the binding constant of the proteinrligand interaction can be estimated using 1 D diffusion-edited spectra of the ligand in the presence and absence of protein (A. J. Lennon et al., *Biophys. J.*, 67, 2096 (1994)). If labeled protein is available, a 2D $^1$H-$^{15}$N HSQC spectrum can also be obtained to locate the ligand binding site on the protein (J. Wang et al., *Biochemistry*, 31, 921 (1992); and S. B. Shuker et al, *Science*, 274, 1531 (1996)). In cases where the protein is small enough and structural characterization of the binding interaction is desired, further experiments can be carried out using $^{15}$N and/or $^{13}$C/$^{15}$N protein/ligand complexes.

Figure 16:
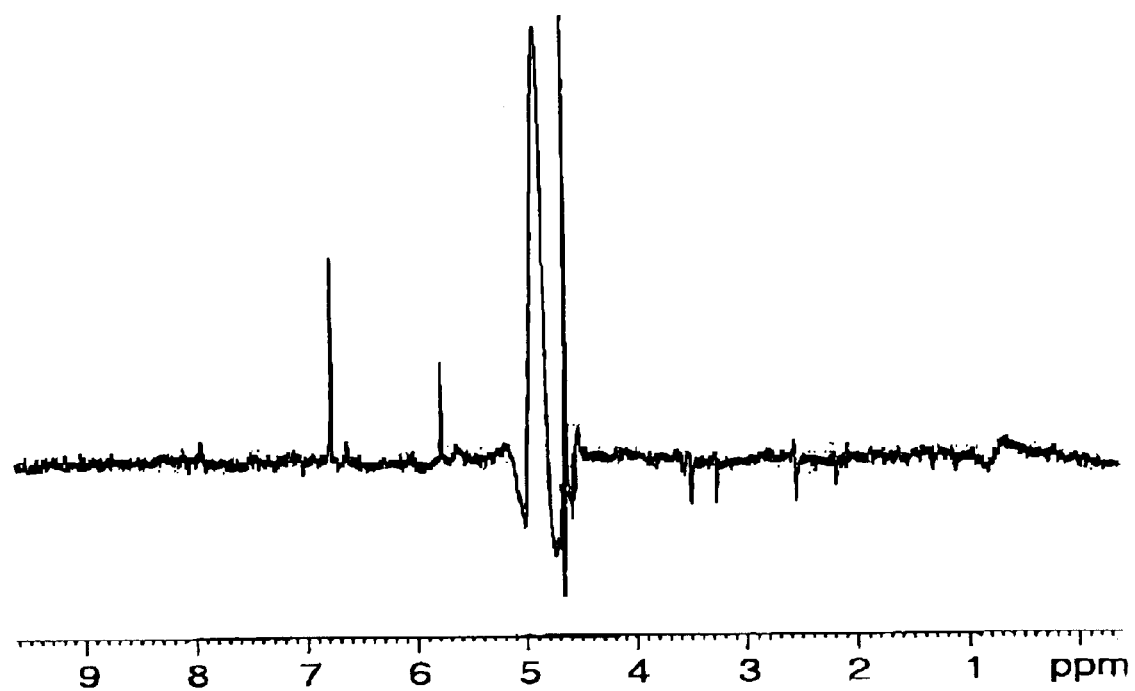
FIG. 16. Region of the 600.13 MHz WaterLOGSY spectrum of a compound mixture with added target protein. The concentration of protein was 10 $\mu$M while the concentration of each compound was 100 $\mu$M. The spectrum was acquired on a Bruker 5 mm flow-injection probe at 27° C. A total of 4K scans were collected resulting in a total acquisition time of about 288 minutes. A mixing time of 2.0 seconds was used.

When binding is detected using the WaterLOGSY technique, sample preparation and use of the flow-injection apparatus is identical, except that extremely low levels of target are used (1–10 $\mu$M) with ratios of ligand to target of 100:1 to 10:1. For data analysis, binding compounds are distinguished from nonbinders by the opposite sign of their water-ligand NOEs. In contrast to the relaxation-edited technique, only a single WaterLOGSY spectrum is used for each ligand mixture. There is no need to collect a reference spectrum in the absence of target protein. An example is illustrated in FIG. 16 for a mixture of compounds and a different protein. In the WaterLOGSY spectrum shown in FIG. 16, binding compounds have resonances of opposite intensity (sharp positive peaks) than nonbinders (near zero intensity or sharp negative peaks). Residual protein resonances are also of positive intensity.

Data Analysis

The development of flow probes has facilitated the transition to high-throughput NMR and has made possible the routine collection of tremendous volumes of data. Recent software developments have advanced the automated handling of large data sets collected on combinatorial chemistry libraries (P. A. Keifer et al., *J. Comb. Chem.*, 2, 151 (2000);

Bruker Instruments, AMIX, BEST and ICONNMR software packages; Varian NMR Systems, VNMR software package; and Williams A, Book of Abstracts, 218th ACS National Meeting (1999)). Visualization of results in a 96-well format allows rapid evaluation of the data sets. The integration of features such as this into a software package tailored more for data reduction and evaluation of library screening data sets parallels the combinatorial chemistry software development but remains slightly behind. However, recent advancements that have been made for combinatorial chemistry data analyses portend similar developments for the automation of protein binding screening data.

In our 1D relaxation-edited $^1$H NMR data sets, one can simply identify the ligand resonances by inspection since their intensity is reduced in the presence of protein as shown in FIG. 14. In our WaterLOGSY data sets, binding compounds are distinguished from nonbinders by the opposite sign of their water-ligand NOEs as observed in FIG. 15. In either case, comparison to an assigned small molecule control spectrum are made to identify the compound associated with the indicated resonances.

Other labs have relied on difference spectra to analyze relaxation- or diffusion-edited 1D $^1$H NMR data sets (P. J. Hajduk et al., J. Am. Chem. Soc., 119, 12257 (1997); N. Gonnella et al., J. Magn. Reson., 131, 336 (1998); and A. Chen et al., J. Am. Chem. Soc., 122, 414 (2000)). After a series of spectral subtractions, the resulting spectrum represents the resonances of the compounds that bind to the protein. Two factors that pose problems are line broadening and shifting resonances, both of which can lead to subtraction artifacts. Changes in intensity can also add the need for a scaling factor in the data analysis step. These additional steps, which can vary from one spectra to the next, make strategies for automated data analysis complex.

Data analysis for 2D screening methods typically involves either the analysis of protein chemical shift perturbations indicative of ligand binding (A. Ross et al., J. Biomol. NMR, 16, 139 (2000); and S. B. Shuker et al, Science, 274, 1531 (1996)), or the analysis of changes in signals from the small molecules in NOE or DECODES spectra indicative of binding (B. Meyer et al., Eur. J. Biochem., 246, 705 (1997); J. Fejzo et al., Chem. Biol., 6, 755 (1999); and M. Lin et al., J. Am. Chem. Soc., 119, 5249 (1997)). While a series of 2D $^1$H-$^{15}$N HSQC spectra can be compared manually, automated analysis using both non-statistical and statistical approaches of a series of $^1$H-$^{15}$N HSQC spectra acquired with flow-injection NMR methods was recently demonstrated (A. Ross et al., J. Biomol. NMR, 16, 139 (2000)). AMIX was used for the non-statistical analysis by comparing spectra collected in the presence of single compounds to the reference spectrum of the protein alone. Then, using bucketing calculations for data reduction, a table ranked by the correlation coefficient was generated. No correlations were observed using the bucketing calculations alone. Subsequently, integration patterns for all 300 small molecule spectra were analyzed by AMIX to generate a data matrix of N integration regions times 300. A statistical software package, UNSCRAMBLER 6.0, was then used to analyze this data matrix using principal components analysis. Two classes of spectral changes were observed. Ultimately, one class was found to correspond to pH changes caused by certain small molecules while the other class corresponded to small molecules binding to the target protein (A. Ross et al., J. Biomol. NMR, 16, 139 (2000)).

Data reduction is an important aspect for handling the amounts of data generated if high-throughput screening by NMR is to be successful. Non-statistical methods such as the bucketing calculations of AMIX (Bruker Instruments, AMIX, BEST and ICONNMR software packages) or the database comparisons of ACD (Williams A, Book of Abstracts, 218th ACS National Meeting (1999)) compare chemical shift, multiplicity, integration regions and patterns to give correlation factors between spectra. These software packages can be used for data reduction of both one- and two-dimensional data. Prediction software is also available to help aid in interpretation of data sets. Statistical methods such as principal components analysis can be used to analyze data for other correlations that are not apparent using non-statistical methods alone. In the case of 2D $^1$H-$^{15}$N HSQC data, an adaptive, multivariate method that incorporates a weighted mapping of perturbations to correlate information within a spectrum or across many spectra has also been described (F. Delaglio, CHI Conference on NMR Technologies: Development and Applications for Drug Discovery, Baltimore, Md., 4–5 November 1999).

Comparison of Flow vs. Traditional Methods

The advantage of working with samples in the flow NMR screening environment is that each set of spectra are collected on samples that are at the same concentration. This accelerates spectral acquisition considerably. Since the samples are fairly homogeneous, many of the routine tasks need to be completed on only the first sample: probe tuning, $^1$H 90° pulse calibration, receiver gain, number of transients, locking, and gradient shimming. On subsequent samples, these steps can be omitted, although simplex shimming of $Z_1$ and $Z_2$ can still be used with multi-day acquisitions.

Prerequisites for a high-throughput assay include rapid data collection, sample-to-sample integrity and minimal costs. Flow NMR techniques have been developed with each in mind. For 1D $^1$H NMR screening experiments, the process of removing the previous sample from the flow cell, rinsing the flow cell, injecting the next sample, allowing for thermal equilibration, automating solvent suppression and acquiring the data can take less than 10 minutes. In practice, the use of this procedure is two to three times faster than a sample changer with conventional NMR tubes. If compounds were screened in mixtures of 10, this results in a throughput of about 1,500 compounds per day. Use of a liquid handler, such as the Gilson 215 typically employed by Bruker and Varian flow NMR systems, can simplify the preparation of samples as well. Ross and coworkers have demonstrated on-the-fly sample preparation by using the liquid handler to mix the protein to be screened with the small molecule immediately prior to injection (A. Ross et al., J. Biomol. NMR, 16, 139 (2000)). Sample conditions can thus be highly standardized with the resulting spectra very consistent and reproducible. Even if target protein is added manually to pre-plated screening libraries, the amount of pipetting is still less than if using NMR tubes. Recurring expenses associated with purchasing and/or cleaning NMR tubes are eliminated with flow-injection NMR methods. The cost of the 96-well microtitre plates is insignificant compared to NMR tubes.

In other embodiments, the methodologies described above also can be used to determine the potential biological roles of proteins having previously unknown function. In today's era of high throughput genome sequencing, complete genomes of tens of organisms have already been sequenced and work on hundreds more is in progress. This has led to identification of thousands of new proteins. The potential of these proteins to act as drug targets cannot be fully assessed without the knowledge of the protein's function and importance in biological processes.

Historically, functional assays, such as those described above, have been used to identify compounds that bind to proteins having known function (drug targets), which eventually become drug candidates. The NMR binding assays described above can be used to identify compounds that bind to proteins of unknown function. Identifying which types of compounds bind to a protein can help in understanding the previously unknown biological and/or biochemical function of the protein. Specific interactions between macromolecules and smaller molecular weight ligands are important in all biochemical processes. Enzymes require specific binding of cofactors and/or substrates to carry out the reactions that they catalyze. Inhibitors are designed to specifically bind enzymes and receptors in or around the active site, and they often are analogous to substrates or cofactors.

Specific interactions are necessary for the proteins to carry out their functions. Hence, identifying which compounds bind to proteins of unknown function can provide clues about that protein's function. For example, a hypothetical protein function may be by identified by characterizing those compounds that bind to the protein in terms of their function as inhibitors, cofactors, or substrates of known proteins. NMR based binding assays can be used to identify which ligands in a screening library bind to the protein. Knowing what types of ligands bind to the protein helps to estimate the protein's function, which in turn, facilitates analyzing the protein's potential as a drug target by creating a target priority list.

Screening Library Design

Several databases were searched to find known inhibitors, cofactors, and substrates of known proteins. Four hundred and thirty compounds were compiled through these searches. Small amounts (about 2–5 mgs.) of 220 compounds were obtained internally or from Sigma/Aldrich. All these compounds were tested for solubility and purity. The solubility tests involved assessment of the compounds to make a 50 mM stock solution in either DMSO or 100 mM phosphate buffer, pH 6.5. The solubility of the compounds was also tested at 100 $\mu$M concentration in 100 mM phosphate buffer pH 6.5, which is a typical NMR binding assay condition. The purity of the compounds was checked by mass spectrometry and NMR spectroscopy.

The screening library finally contained 156 compounds, all of which passed the solubility and purity tests. These compounds had a range molecular weights from 46 to 1389 with average molecular weight being 301. These compounds are also known to interact with a wide spread of enzyme classes covering a broad spectrum of metabolic pathways. Table 1 describes the distribution of the library compounds over the major enzyme classes. Of course, it is possible to add more compounds to this library as they are identified by their interactions with known proteins.

TABLE 1

Distribution of compounds over major enzyme classes.

| Enzyme class | Enzyme type | Number of compounds |
| --- | --- | --- |
| 1 | Oxidoreductases | 60 |
| 2 | Transferases | 34 |
| 3 | Hydrolases | 56 |
| 4 | Lyases | 32 |
| 5 | Isomerases | 13 |

Preparation of Mixtures

To improve screening efficiency, the library was compressed into 30 mixtures, each containing 4 to 7 compounds. The criteria for inclusion of compounds in the mixtures were non-reactivity with each other, and presence of at least one unique resonance corresponding to each compound in the NMR spectrum of the mixture. The NMR spectra of each compound in the mixture were added together to create a theoretical spectrum of the mixture and it was compared with the actual NMR spectrum of the mixture. All theoretical and experimental spectra were consistent with each other indicating non-reactivity of the compounds in the mixtures. There were two types of mixtures depending on compounds that were dissolved in DMSO or buffer to make stock solutions. The mixtures were prepared in 96 well plates, and stored at −80° C. till they were used for screening experiments.

Validation of Library

Several proteins with known functions were used for validating the screening library. The proteins used for validation are listed in Table 2. The proteins were dissolved in 100 mM phosphate buffer, pH 6.5 to make stock solutions which were further diluted and mixed with the compound mixtures to make final concentration of 5–7 $\mu$M. The concentration of compounds was about 133 $\mu$M in the final solution. The ratio of compound to protein concentrations was about 20:1.

TABLE 2

Test proteins used in validation of the library.

| Protein | Molecular weight (kDa) |
| --- | --- |
| γ-Chymotrypsin | 22 |
| Alcohol dehydrogenase | 80 |
| Carbonic anhydrase | 29 |
| Thrombin | 34 |
| Camphor Cytochrome P450 | 47 |
| Transketolase | 74 |
| Lactate dehydrogenase | 45 |

NMR Screening Experiments

NMR experiments for validating the functional genomics library with proteins of known functions were conducted on a Bruker Avance 600 MHz spectrometer equipped with 5 mm FISEI flow probe and Gilson 215 liquid sample handler. Binding was detected using the WaterLOGSY experiment.

Results from Thrombin Screening Experiments

Figure 17:
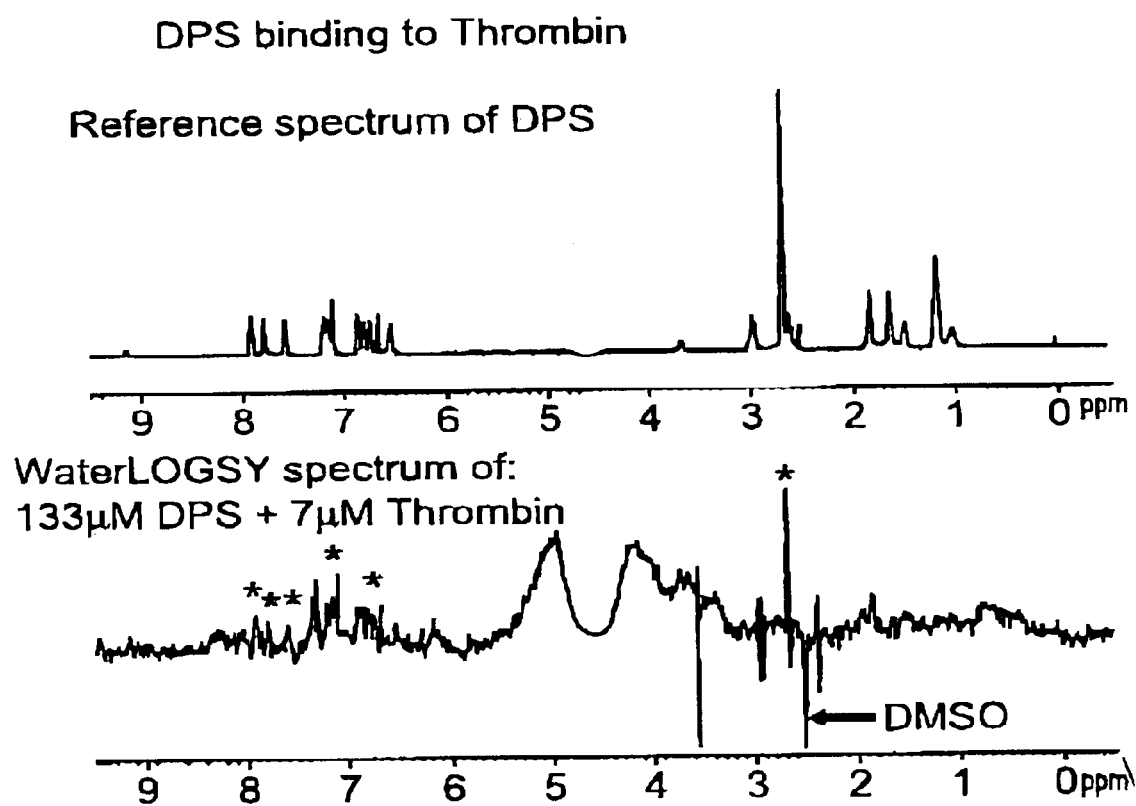
FIG. 17. Comparison of WaterLOGSY spectrum (bottom panel) of thrombin with a compound mixture of the genomics screening library and the reference spectrum of DPS (top panel).

The functional genomics screening library was screened against thrombin obtained from Sigma, which is one of the test proteins used for validation of the library. One assay mixture contained 133 $\mu$M of N-alpha-dansyl-DL-tryptophan cyclohexylammonium salt (DPS) and 7 $\mu$M of thrombin in 100 mM phosphate buffer, pH6.5. This mixture also contained Benzyl (S)-(−)-2-(1-pyrrolidinylcarbonyl)-1-pyrrolidinecarboxylate (ZPR), Chymostatin A (CSA), Tetrahydrofolic acid (C2F), Haloperidol (THK). Referring to FIG. 17, the reference NMR spectrum of DPS is in the top panel while the WaterLOGSY spectrum of the mixture is shown in the bottom panel. The positive peak in the WaterLOGSY spectrum indicates binding of DPS to thrombin. The peaks indicated by red asterisks in the WaterLOGSY spectrum correspond to peaks from the reference spectrum of DPS shown in the top panel.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein. Such examples and embodiments are presented by way of example only with the scope of the invention intended to be limited only by the claims set forth herein as follows.

What is claimed is:

1. A method of identifying a function of a target molecule, the method comprising:

providing a plurality of mixtures of test compounds consisting of known inhibitors, cofactors, and substrates of known proteins, each mixture being in a sample reservoir and containing a plurality of test compounds;

introducing a target molecule of unknown function into each of the sample reservoirs to provide a plurality of test samples;

providing a nuclear magnetic resonance spectrometer equipped with a flow-injection probe;

transferring each test sample from the sample reservoir into the flow-injection probe;

collecting a WaterLOGSY nuclear magnetic resonance spectrum on each sample in each reservoir, comparing the spectra of each sample to the spectra taken under the same conditions in the absence of the target molecule to identify compounds that bind to the target molecule, wherein the concentration of target molecule and each compound in each sample is no greater than about 100 $\mu$M; and determining a function of the target molecule based upon the test compounds that bind to the target molecule.

2. The method of claim 1 wherein the concentration of target molecule in each sample is no greater than about 10$\mu$.

3. The method of claim 2 wherein the concentration of target molecule is no greater than about 1 $\mu$M.

4. The method of claim 1 wherein the concentration of each test compound in each sample reservoir is no greater than about 100 $\mu$M.

5. The method of claim 1 wherein each test compound has a solvability in deuterated water of at least about 1 mM at room temperature.

6. The method of claim 1 wherein collecting a Water-LOGSY nuclear magnetic resonance spectrum comprises collecting a 1D WaterLOGSY nuclear magnetic resonance spectrum.

7. The method of claim 1 wherein the mixture of test compounds comprises at least about 3 compounds, each having at least one distinguishable resonance in a 1D NMR spectrum of the mixture.

8. The method of claim 1 wherein the ratio of each test compound to target molecule in each sample reservoir is about 100:1 to about 10:1.

9. The method of claim 1 wherein the target molecule is a protein.

* * * * *

UNITED STATES PATENT AND TRADEMARK OFFICE
CERTIFICATE OF CORRECTION

PATENT NO.     : 6,764,858 B2
DATED          : July 20, 2004
INVENTOR(S)    : Brian J. Stockman It is certified that error appears in the above-identified patent and that said Letters Patent is hereby corrected as shown below:

Title page,
Item [56], References Cited, OTHER PUBLICATIONS,
"Hedge et al. (1992)" reference, delete "1.7 •" and replace with -- 1.7 Å --.
"Stockman, Baltimore, MD (1999)" reference, after the word "binding" delete "fo" and replace with -- of --.

Column 6,
Line 35, delete "3indoleacrylate" and replace with -- 3-indoleacrylate --.
Lines 38 and 46, delete "10compound" and replace with -- 10-compound --.
Line 51, after "19º" and before the word "excitation" insert -- C with pulsed field gradients tilted at the magic angle for better solvent suppression. The --.
Line 60, delete "EMBODIMENT" and replace with -- EMBODIMENTS --.

Column 10,
Line 17, delete "Dalvitet" and replace with -- Dalvit et. --.
Line 18, delete "Otting et a)." and replace with -- Otting et al. --.
Line 31, delete "(1995):" and replace with -- (1995); --.
Line 32, delete "(1996):" and replace with -- (1996); --.
Line 33, delete "(1999a):" and replace with -- (1999a); --.

Column 11,
Line 15, delete "urn" and replace with -- $\mu$m --.

Column 12,
Line 24, delete "1H" and replace with -- $^1$H --.

Column 16,
Line 1, delete "al.0x10$^{-6}$M" and replace with -- 1.0x10$^{-6}$M --.

Column 18,
Line 5, delete "(1998)" and replace with -- (1998)) --.
Line 7, after "resonances (" insert -- J. Wang et al., *Biochemistry*, 31, 921 (1992)), or line broadening (D.L. Rabenstein et al., --.
Line 8, after "T. Scherf et al.," insert -- *Biophys. J.*, 64, 754 (1993)), change in sign of the NOE from positive to negative (P. Balaram et al., --.
Line 15, delete "(s.B." and replace with -- (S.B. --.
Line 17, delete "(1997), Meyer et al." and replace with -- (1997)), Meyer (B. Meyer et al. --.
Line 18, delete "(1997)." and replace with -- (1997)), --.

UNITED STATES PATENT AND TRADEMARK OFFICE
CERTIFICATE OF CORRECTION

PATENT NO. : 6,764,858 B2
DATED : July 20, 2004
INVENTOR(S) : Brian J. Stockman

It is certified that error appears in the above-identified patent and that said Letters Patent is hereby corrected as shown below:

Column 24,
Line 34, delete "proteinrligand" and replace with -- protein/ligand --.
Line 35, delete "1  D" and replace with -- 1D --.

Column 30,
Line 11, delete "solvability" and replace with -- solubility --.

Signed and Sealed this

Seventh Day of June, 2005

JON W. DUDAS
*Director of the United States Patent and Trademark Office*